United States Patent [19]

Muchowski et al.

[11] 3,997,587
[45] Dec. 14, 1976

[54] D1- AND 8R-9-FLUORO-PROSTADIENOIC ACID DERIVATIVES

[75] Inventors: Joseph M. Muchowski; Esperanza V. Velarde, both of Mexico City, Mexico

[73] Assignee: Syntex (U.S.A.) Inc., Palo Alto, Calif.

[22] Filed: June 26, 1975

[21] Appl. No.: 590,661

[52] U.S. Cl. .................... 260/468D; 260/240 R; 260/256; 260/448 R; 260/501.1; 260/501.17; 260/501.2; 260/514 D; 424/305; 424/317
[51] Int. Cl.$^2$ ...................... C07C 177/00
[58] Field of Search .................. 260/468 D, 514 D

[56] References Cited

OTHER PUBLICATIONS

Sharts et al., Organic Reactions 21, p. 158, (1974).

Primary Examiner—Robert Gerstl
Attorney, Agent, or Firm—Gerard A. Blaufarb; William B. Walker

[57] ABSTRACT dl- and 8R-9-fluoro-11,15α-dihydroxyprosta-5-cis,13-trans-dienoic acid, dl- and 8R-9-fluoro-11,15α-dihydroxy-15β-methyl-prosta-5-cis,13-trans-dienoic acid and dl- and 8R-9-fluoro-11,15β-dihydroxy-15α-methylprosta-5-cis,13-trans-dienoic acid, the pharmaceutically acceptable, nontoxic lower alkyl esters and salts thereof and process for the production of such compounds. 8R-9β-fluoro-11α,15α-dihydroxyprosta-5-cis,13-trans-dienoic acid is a representative compound of the class. These compounds possess prostaglandin-like activities and thus are useful in the treatment of mammals where prostaglandins are indicated. They are particularly useful as luteolytic agents in female mammals and as bronchodilators.

41 Claims, No Drawings

DL- AND 8R-9-FLUORO-PROSTADIENOIC ACID DERIVATIVES

The present invention relates to certain novel prostaglandin analogs and to process for the production thereof.

More particularly, the present invention relates to dl- and 8R-9-fluoro-11,15α-dihydroxyprosta-5-cis,13-trans-dienoic acids, dl- and 8R-9-fluoro-11,15α-dihydroxy-15β-methylprosta-5-cis,13-trans-dienoic acids, dl- and 8R-9-fluoro-11,15β-dihydroxy-15α-methylprosta-5-cis,13-transdienoic acids, the pharmaceutically acceptable, non-toxic lower alkyl esters and salts thereof and to the process for producing such compounds.

Prostaglandins have classically been described as chemically related 20 carbon chain hydroxy fatty acids having the basic skeleton of prostanoic acid:

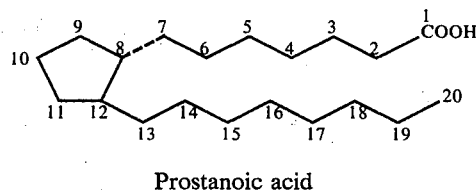

Prostanoic acid

The prostaglandins having a hydroxyl group at the C-11 position and an oxo group at the C-9 position are known as the PGE series, those having a hydroxyl group in place of the oxo group are known as the PGF series and are further designated by an α or β suffix to indicate the configuration of the hydroxyl group at said position. The natural compounds are the α-hydroxy substituted compounds. They may contain different degrees of unsaturation in the molecule, particularly at C-5, C-13 and C-17, the unsaturation is also indicated by a suffix. Thus for example, the $PGF_1$ and $PGE_1$ series refer to prostanoic acids having a trans olefin bond at the C-13 position, while the $PGF_2$ and $PGE_2$ series refer to prostadienoic acids having a cis-olefin bond at the C-5 position and a trans olefin bond at the C-13 position. For a review on prostaglandins and the definition of primary prostaglandins, see, for example, S. Bergström, Recent Progress in Hormone Research 22, pp. 153–175 (1966) and Science 157, page 382 (1967) by the same author.

The preparation of derivatives of prostanoic acid has become of great importance since the demonstration of the highly interesting range of biological and pharmacological activities of natural prostaglandins.

The great majority of these studies have focused on modification of the two side chains, or modifications of the substituents attached to the cyclopentane moiety [see for example U. Axen et al., Synthesis Vol. 1, John Wiley and Sons Inc., New York, N.Y. (1973) and P. H. Bently, Chem. Soc. Reviews 2, 29 (1973)].

In accordance with the present invention we have prepared certain novel dl- and 8R-9-fluoro-prostaglandin analogs represented by the following formulas:

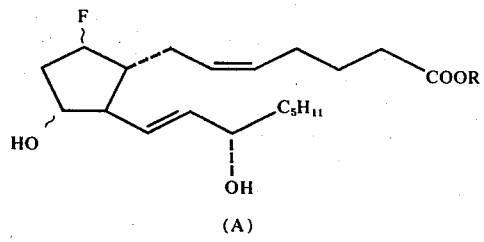 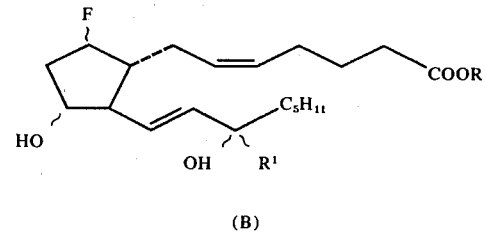

(A)    (B)

wherein R is hydrogen, a lower alkyl group of one to six carbon atoms, or the pharmaceutically acceptable, non-toxic salts of compounds in which R is hydrogen; $R^1$ is methyl or ethyl; and the wavy lines (⌇) represent the α or β configuration or mixtures thereof, provided that when $R^1$ is α, the hydroxyl group, attached to the same carbon atom as $R^1$, is β; and when $R^1$ is β, the hydroxyl group, attached to the same carbon as $R^1$, is α.

The dashed lines (⋮) shown in the above formulas and in the formulas below indicate that the substituents are in α configuration, i.e., below the plane of the cyclopentane ring, while the heavy lines (▼) indicate that the substituents are in β-configuration, i.e., above the plane of the cyclopentane ring.

The double bonds at C-5 and C-13 in the compounds of the present invention have the same configuration as in natural prostaglandins of the PGE and PGF series, that is the cis and trans configurations, respectively.

When the compounds of the present invention are racemic mixtures, i.e., dl compounds, they are produced starting from racemic mixtures, while when the compounds of the invention are individual antimers, i.e., 8R compounds, they are obtained starting from the appropriate individual 8R-antimer.

For the sake of simplicity only one antimer of each pair will be depicted in the description of the process and claims; however, it is to be understood that the mirror images for the racemic mixtures and the individual antimers are also encompassed thereby.

The use of the symbol "8R" preceding the compound names designates the absolute stereochemistry at that position according to the Cahn-Ingold-Prelog rules [see Cahn et al., Angew, Chem. Inter. Edit., Vol. 5, p. 385 (1966), errata p. 511; Cahn et al., Angew. Chem., 78, p. 413 (1966); Cahn and Ingold, J. Chem. Soc., (London), 1951, p. 612; Cahn et al., Expirientia, Vol. 12, p. 81 (1956); Cahn J. Chem. Educ., Vol. 41, p. 116 (1964)]. Because of the interrelation of the 8R designation with the other substituents in a compound, having α or β prefixes, the designation of the absolute configuration as 8R fixes the absolute configuration of all substituents in the compound and thus the absolute configuration of the compound as a whole.

The term "lower alkyl" as used herein refers to straight or branched alkyl groups containing up to 6 carbon atoms, e.g., methyl, ethyl, n-propyl, isopropyl, n-butyl, t-butyl, pentyl, isopentyl, hexyl, isohexyl and the like.

The term "pharmaceutically acceptable salts" refers to salts prepared from pharmaceutically acceptable nontoxic bases, including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic nontoxic bases are isopropylamine, diethylamine, ethanolamine, piperidine, tromethamine, choline and caffeine.

The prostaglandin analogs of the present invention can be obtained by a process illustrated by the following sequence of reactions:

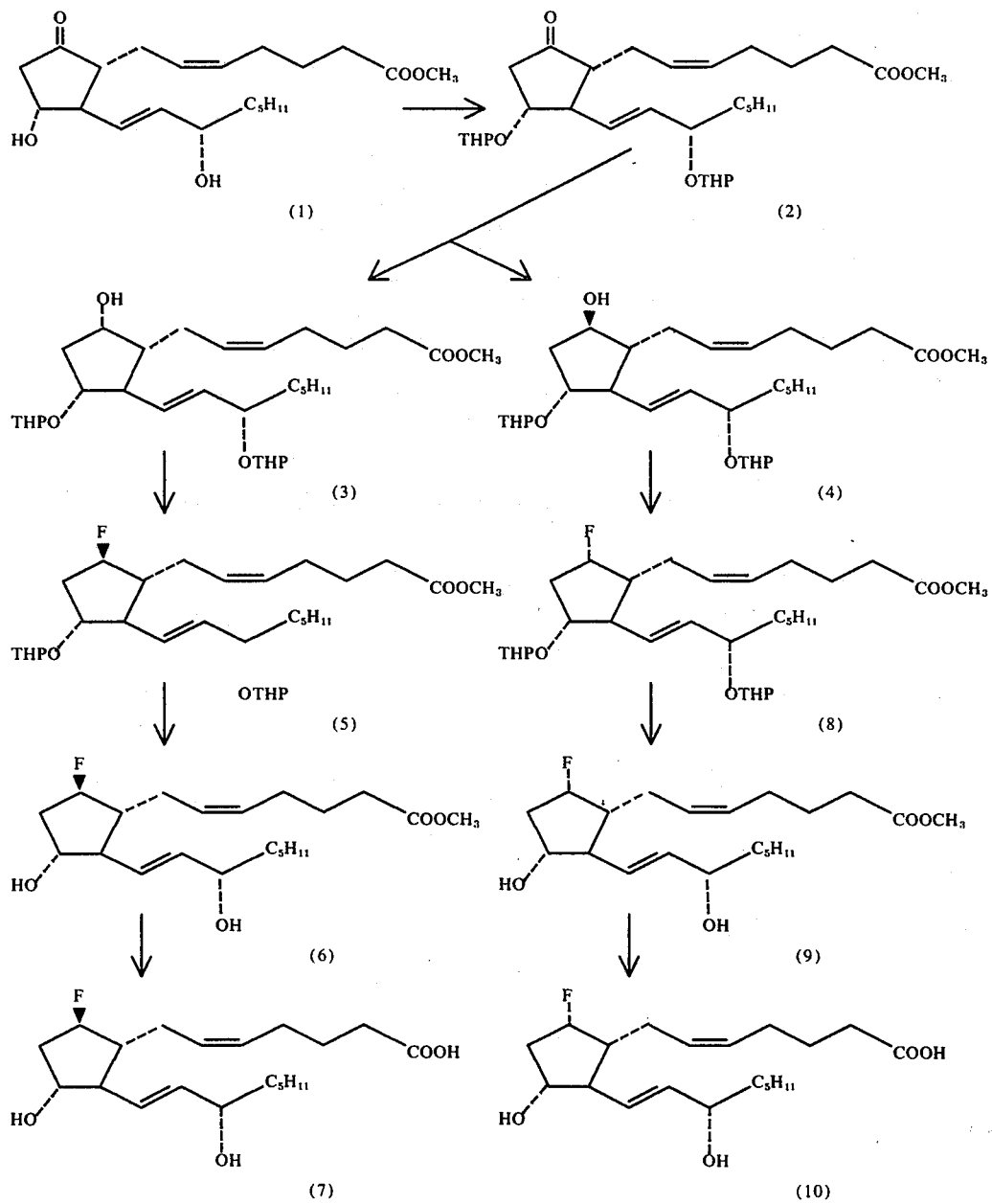

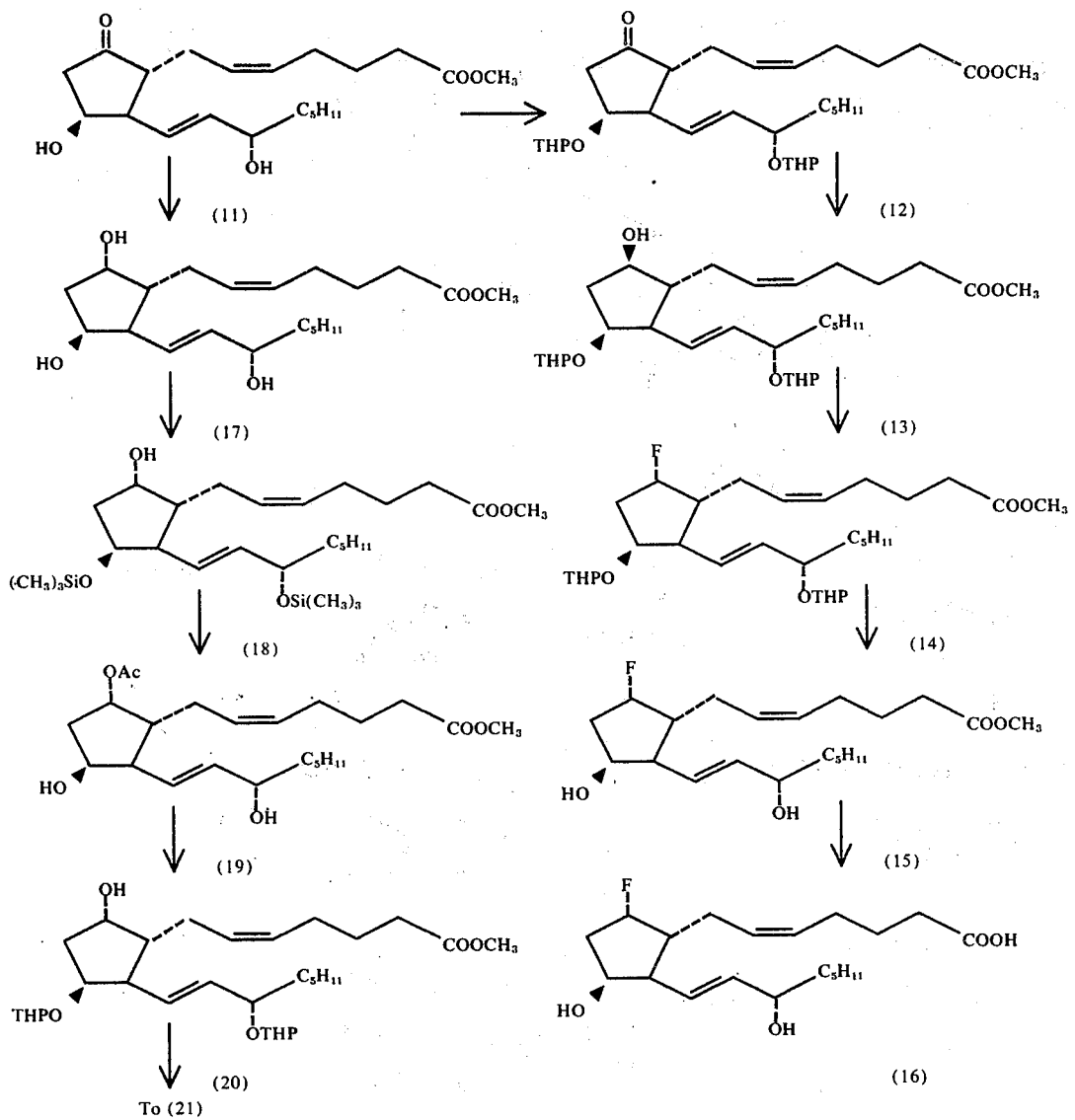
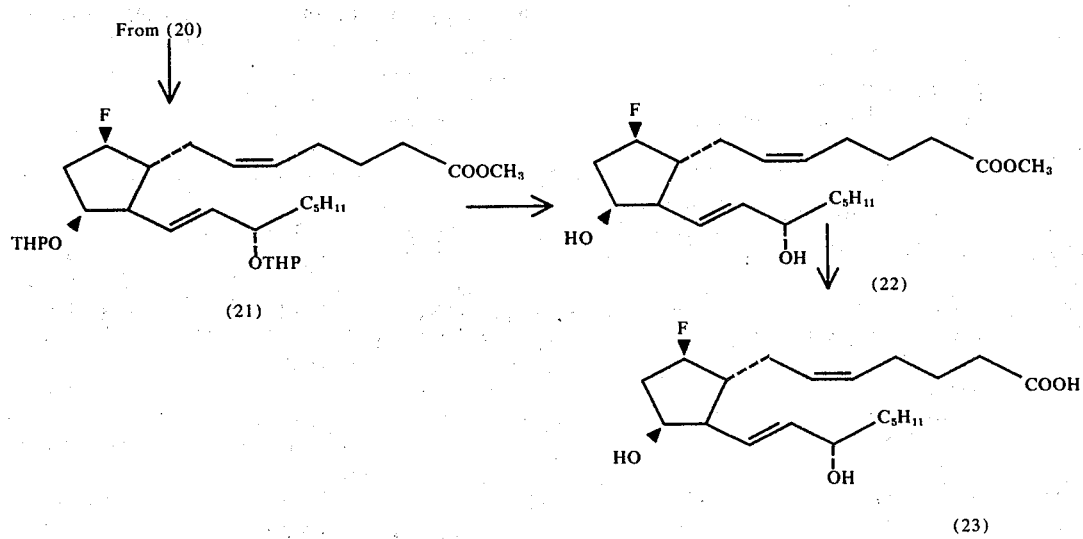

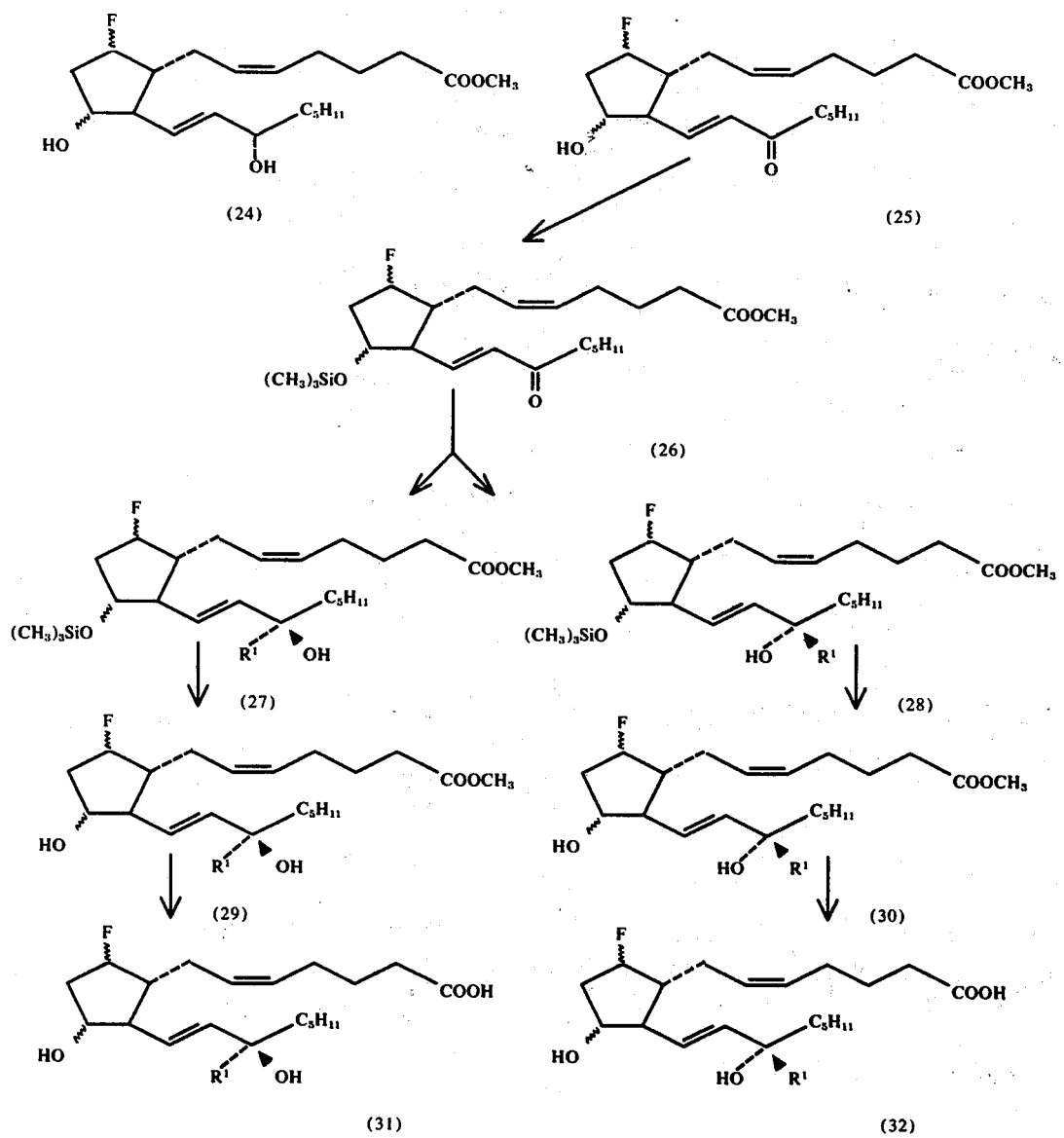

wherein THP is tetrahydropyran-2-yl;
Ac is acetyl;
R¹ is methyl or ethyl; and
the wavy line is defined as above.

In the specification and examples which follow, where purification of, and/or separation of, compounds is desired, it can be achieved by techniques well-known to those skilled in the art, e.g., column chromatography, thin layer chromatography, extraction, evaporation, crystallization, filtration, decantation, and the like, or a combination thereof. For a more detailed description of the purification, and/or separation, techniques employed, reference may be had to the examples.

In practicing the invention depicted by the reaction scheme above, the dl-prostaglandin or 8R-prostaglandin (described in U.S. Pat. No. 3,772,350, which is hereby incorporated by reference) of Formula (1) is etherified to the corresponding 11α,15α-bis-(tetrahydropyran-2-yloxy) compound of Formula (2). This reaction is carried out in a conventional manner by reacting the compound of Formula (1) with dihydropyran, in the presence of an organic solvent, and p-toluenesulfonic acid as catalyst, at a temperature of from about 0° to about 30° C., for from about 10 minutes to about 30 minutes. Suitable organic solvents are dichloromethane, benzene, chloroform, and the like.

The compound of Formula (2) is then treated with a reducing agent to convert the 9-oxo to the 9-hydroxy group, two isomers, the 9α-hydroxy compound of Formula (3) and the 9β-hydroxy compound of Formula (4), being obtained. The reduction is carried out by treating the compound of Formula (2) with a double metal hydride, e.g., sodium borohydride, lithium tri-t-butoxyaluminum hydride, zinc borohydride, and the like, in the presence of, an organic solvent, e.g., methanol, tetrahydrofuran, dimethoxyethane, diethyl ether, and the like, at a temperature of from about −40° to about 25° C., for from about 15 minutes to about three hours. The 9α-hydroxy compound of Formula (3) and 9β-hydroxy compound of Formula (4) are separated by conventional techniques.

Alternatively, the compound of Formula (3) is obtained by treating the compound of Formula (2) with potassium tri-sec-butylborohydride (prepared in situ from lithium tri-sec-butyl borohydride and dry potassium chloride), under an inert atmosphere and in the presence of an organic solvent, e.g., tetrahydrofuran, dimethoxyethane, diethylether, and the like, at a temperature of from about −80° to about 0° C., for from about 5 minutes to about 1 hour.

The 9α-hydroxy compound of Formula (3) is treated with a fluorinating agent, capable of replacing a secondary hydroxyl group with a fluorine atom, in an anhydrous organic solvent, to obtain the 9β-fluoro compound of Formula (5). Suitable fluorinating agents are N(2-chloro-1,1,2-trifluoroethyl)diethylamine, N(2-chloro-1,1,2-trifluoroethyl)dimethylamine, N(1,1,2,2-tetrafluoroethyl)diethylamine, and the like. The preferred fluorinating agent is N(2-chloro-1,1,2-trifluoroethyl)diethylamine, and its reaction with the compound of Formula (3) is carried out in the presence of an organic solvent, e.g., dichloromethane, diethyl ether, tetrahydrofuran, and the like, or mixtures thereof, at a temperature of from about −20° to about 0° C., for from about three hours to about seven hours, using from 1.5 to 2 molar equivalents of the reagent, particularly 1.75 molar equivalents per mol of a compound of Formula (3).

The compound of Formula (6) is obtained by deetherifying the compound of Formula (5). The deetherification is carried out according to methods well-known in the art, and preferably by treating the compound of Formula (5) with an aqueous mild acid, e.g., acetic, oxalic, tartaric, and the like, at a temperature of from about 10° to about 40° C., preferably at room temperature, for from about eight hours to about 16 hours, using 65% aqueous acetic acid.

The compound of Formula (7) is obtained by deesterifying the compound of Formula (6). The deesterification is carried out according to methods well-known in the art, and preferably by treating the compound of Formula (6) with a base, e.g., potassium carbonate, sodium carbonate, sodium hydroxide, potassium hydroxide, and the like, at a temperature of from about 0° to about 50° C. for from about 18 hours to about 80 hours.

The 9β-hydroxy compound of Formula (4) is treated with a fluorinating agent, capable of replacing a secondary hydroxyl group with a fluorine atom, in an anhydrous organic solvent, to obtain the 9β-fluoro compound of Formula (8). Suitable fluorinating agents are N-(2-chloro-1,1,2-trifluoroethyl)diethylamine, N(1,1,1,2-tetrafluoroethyl)diethylamine, N-(2-chloro-1,1,2-trifluoroethyl)dimethylamine, and the like. The preferred fluorinating agent is N(2-chloro-1,1,2-trifluoroethyl)diethylamine, and its reaction with the compound of Formula (4) is carried out in the presence of an anhydrous organic solvent, e.g., dichloromethane, diethylether, tetrahydrofuran, and the like, or mixtures thereof, at a temperature of from about −20° to about 0° C., for from about three hours to about seven hours.

The compound of Formula (9) is obtained by deetherifying the compound of Formula (8). The deetherification is carried out according to methods well-known in the art, and preferably by treating the compound of Formula (8) with an aqueous weak acid, e.g., acetic, oxalic, tartaric, and the like, at a temperature of from about 10° to about 40° C. for from about eight hours to about 16 hours.

The compound of Formula (10) is obtained by deesterifying the compound of Formula (9). The deesterification is carried out by according to methods well-known in the art, and preferably by treating the compound of Formula (9) with a base, e.g., potassium carbonate, sodium carbonate, sodium hydroxide, potassium hydroxide, and the like, at a temperature of from about 0° to about 40° C. for from about 18 hours to about 60 hours.

The dl-prostaglandin or 8R-prostaglandin (described in U.S. Pat. No. 3,772,350) of Formula (11) is converted to the corresponding 11β,15α-bis-(tetrahydropyran-2-yloxy) compound of Formula (12). This reaction is carried out in a conventional manner by reacting the compound of Formula (11) with dihydropyran, in the presence of an organic solvent, and p-toluenesulfonic acid as catalyst, at a temperature of from about 0° to about 30° C., for from about ten minutes to about 30 minutes. Suitable organic solvents are dichloromethane, benzene, chloroform, and the like.

The compound of Formula (12) is then treated with a reducing agent to convert the 9-oxo to the 9β-hydroxy group, thus obtaining the compound of Formula (13). The reduction is carried out by treating the compound of Formula (12) with sodium borohydride, zinc borohydride, lithium tri-t-butoxyaluminum hydride, and the like in the presence of, an organic solvent, e.g., methanol, tetrahydrofuran, dimethoxyethane, diethylether, and the like, at a temperature of from about −40° to about 25° C., for from about 20 minutes to about three hours.

The 9β-hydroxy compound of Formula (13) is treated with a fluorinating agent, capable of replacing a secondary hydroxyl group with a fluorine atom, in an anhydrous organic solvent, to obtain the 9α-fluoro compound of Formula (14). Suitable fluorinating agents are N(2-chloro-1,1,2-trifluoroethyl)diethylamine, N(1,1,1,2-tetrafluoroethyl)diethylamine, N(2-chloro-1,1,2-trifluoroethyl)dimethylamine, and the like. The preferred fluorinating agent is N(2-chloro-1,1,2-trifluoroethyl)diethylamine, and its reaction with the compound of Formula (13) is carried out in the presence of an organic solvent, e.g., dichloromethane, diethyl ether, tetrahydrofuran, and the like, or mixtures thereof, at a temperature of from about −20° to about 0° C., for from about 3 hours to about seven hours.

The compound of Formula (15) is obtained by deetherifying the compound of Formula (14). The deetherification is carried out according to methods well-known in the art, and preferably by treating the compound of Formula (14) with an aqueous weak acid, e.g., acetic, oxalic, tartaric, and the like, at a temperature of from about 10° to about 40° C. for from about eight hours to about 16 hours, using particularly 65% aqueous acetic acid.

The compound of Formula (16) is obtained by deesterifying the compound of Formula (15). The deesterification is carried out according to methods well-known in the art, and preferably by treating the compound of Formula (15) with a base, e.g., potassium carbonate, sodium carbonate, sodium hydroxide, potassium hydroxide, and the like, at a temperature of from about 0° to about 40° C. for from about 18 hours to about 60 hours.

The dl-prostaglandin or 8R-prostaglandin (described in U.S. Pat. No. 3,772,350) of Formula (11) is reduced to the corresponding 9α,11β,15α-trihydroxy compound of Formula (17), in mixture with the 9β,11β,15α-trihydroxy compound. The reduction of the 9-oxo group is carried out by treating the compound of Formula (11) with sodium borohydride, zinc borohydride, aluminum hydride, and the like, in the presence of an organic solvent, e.g., methanol, diethyl ether, tetrahydrofuran, and the like, at a temperature of from about −40° to about 25° C., for from about 20 minutes to about three hours (time).

The compound of Formula (17) is then silylated to convert the 11β-and 15α-hydroxy groups to the 11β,15α-bis(trimethylsilyloxy) compound of Formula (18). This reaction is carried out by treating the compound of Formula (17) with N-trimethylsilyldiethylamine in the presence of an organic solvent, e.g., acetone, tetrahydrofuran, benzene, and the like, under an inert atmosphere, at a temperature of from about −50° C. to 0° C., for from about 1 hour to about 4 hours.

The 9α-hydroxy group of the compound of Formula (18) is then acetylated, followed by desilylation to give the 9α-acetoxy-11β,15α-dihydroxy compound of Formula (19). The 9α-acetylation is carried out in a conventional manner by treating the compound of Formula (18) with acetic anhydride, in the presence of an organic solvent, e.g., pyridine, 4-dimethylaminopyridine, triethylamine, and the like, at a temperature of from about 0° to about 25° C., for from about 30 minutes to about two hours thus yielding the 9α-acetoxy-11β,15α-bis-(trimethylsilyloxy) compound, which is desilylated by mild acid treatment, e.g., using 5% aqueous glacial acetic acid, in the presence of an organic solvent, e.g., methanol, ethanol, and the like, at a temperature of from about 0° to about 25° C., for from about 45 minutes to about 16 hours.

The 9α-acetoxy-11β,15α-dihydroxy compound of Formula (19) is then conventionally reacted with dihydropyran, in the presence of an organic solvent, e.g., dichloromethane, benzene, chloroform, and the like, or mixtures thereof, and p-toluenesulfonic acid as catalyst, at a temperature of from about 0° to about 30° C., for from about ten minutes to about 30 minutes, to yield the corresponding 9α-acetoxy-11β,15α-bis(tetrahydropyran-2-yloxy) compound, which is then deacetylated by treatment with a base, e.g., potassium carbonate, sodium carbonate, and the like, in the presence of an organic solvent, e.g., methanol, and the like, under an inert atmosphere, at a temperature of from about −10° to about 0° C., for from about 2 hours to about four hours, to yield the 9α-hydroxy-11β,15α-bis-(tetrahydropyran-2-yloxy) compound of Formula (20).

The 9α-hydroxy compound of Formula (20) is treated with a fluorinating agent, capable of replacing a secondary hydroxyl group with a fluorine atom, in an anhydrous organic solvent, to obtain the 9β-fluoro compound of Formula (21). Suitable fluorinating agents are N(2-chloro-1,1,2-trifluoroethyl)diethylamine, N(2-chloro-1,1,2-trifluoroethyl)dimethylamine, N(1,1,2,2-tetrafluoroethyl)diethylamine, and the like. The preferred fluorinating agent is N(2-chloro-1,1,2-trifluoroethyl)diethylamine, and its reaction with the compound of Formula 20 is carried out in the presence of an organic solvent, e.g., dichloromethane, diethyl ether, tetrahydrofuran, and the like, or mixtures thereof, at a temperature of from about −20° to about 0° C., for from about three hours to about seven hours.

The compound of Formula (22) is obtained by deetherifying the compound of Formula (21). The deetherification is carried out according to methods well-known in the art, and preferably by treating the compound of Formula (21) with an aqueous weak acid, e.g., acetic, oxalic, tartaric, and the like, at a temperature of from about 10° to about 40° C. for from about eight hours to about 16 hours.

The compound of Formula (23) is obtained by deesterifying the compound of Formula (22). The deesterification is carried out according to methods well-known in the art, and preferably by treating the compound of Formula (22) with a base, e.g., potassium carbonate, sodium carbonate, sodium hydroxide, potassium hydroxide, and the like, at a temperature of from about 0° to about 40° C. for from about 18 hours to about 60 hours.

The compounds of Formula (24), which formula is a composite of Formulas (6), (9), (15) and (22), are treated with an oxidizing agent to convert the 15α-hydroxy thereof to the 15-oxo group, thus obtaining the compounds of Formula (25). The reaction is carried out by treating the compounds of Formula (24) with 2,3-dichloro-5,6-dicyano-1,4-benzoquinone or manganese dioxide, in an organic solvent, e.g., benzene, dioxane, chloroform, and the like, at about room temperature for from about 16 hours to about 40 hours.

The 15-oxo compounds of Formula (25) are then silylated to convert the 11α-hydroxy group to the corresponding 11α-trimethylsilyloxy group, thus obtaining the compounds of Formula (26). This reaction is carried out by treating the compounds of Formula (25) with N-trimethylsilyldiethylamine, in the presence of an organic solvent, e.g., acetone, tetrahydrofuran, benzene, and the like, under an inert atmosphere, at a temperature of from about 0° to about 25° C., for from about one hour to about four hours.

The compounds of Formula (26) are then treated with a Grignard reagent to convert the 15-oxo group thereof to the respective 15β-hydroxy-15α-methyl (or ethyl) compounds of Formula (27) and 15α-hydroxy-15β-methyl (or ethyl) compounds of Formula (28). Suitable Grignard reagents are methyl (or ethyl) magnesium halides and preferably methyl (or ethyl) magnesium bromide. The reaction is carried out in an inert organic solvent, e.g., tetrahydrofuran, diethyl ether, and the like, or mixtures thereof, at a temperature of from about −70° to about 20° C. for from about one hour to about three hours. The trimethylsilyloxy groups are then hydrolyzed by treatment with an aqueous aliphatic alcohol, e.g., 60% aqueous methanol or ethanol, at a temperature of from about 10° to about 25° C., for about 45 minutes to about 16 hours, to produce the desilylated compounds of Formulas (29) and (30). The 15β-hydroxy-15α-methyl (or ethyl) compounds of Formula (29) are separated from the 15α-hydroxy-15β-methyl (or ethyl) compounds of Formula (30) by column chromatography and the like.

The compounds of Formula (31) [or (32)] are obtained by deesterifying the compounds of Formula (29) [or (30)]. The deesterification is carried out according to methods well-known in the art, and preferably by treating the compound of Formula (29) [or (30)] with a base, e.g., potassium carbonate, sodium carbonate, sodium hydroxide, potassium hydroxide, and the like, at a temperature of from about 15° to about 35° C. for from about 18 hours to about 60 hours.

The compounds of Formulas (7), (10), (16), (23), and the individual isomers embraced by Formulas (31) and (32), can be converted into the corresponding alkyl esters by methods known in the art, i.e., by treatment of the free acid with an excess of a diazoalkane, such as diazoethane or diazopropane in ether or methylene chloride solution, in a conventional manner, or by reaction with the desired lower alkyl iodide in the presence of lithium carbonate, at room temperature.

The salt derivatives of the prostadienoic acids of the present invention can be prepared by treating the corresponding free acids, the compounds of Formulas (7), (10), (16), (23), and the individual isomers embraced by Formulas (31) and (32), with about one molar equivalent of a pharmaceutically acceptable base, including inorganic and organic bases per molar equivalent of free acid. Salts derived from inorganic bases include sodium potassium, lithium, ammonium, calcium, magnesium ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary and tertiary amines, substituted amines, including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purine, piperazine, piperidine, N-ethylpiperidine, polyamine resins and the like. Particularly preferred organic non-toxic bases are isopropylamine, diethylamine, ethanolamine, piperidine, tromethamine, choline and caffeine.

The reaction is conducted in water, alone or in combination with an inert, water-miscible organic solvent, at a temperature of from about 0° C to about 100° C., preferably at room temperature. Typical inert, water-miscible organic solvents include methanol, ethanol, isopropanol, butanol, acetone, dioxane or tetrahydrofuran. The molar ratio of compounds of Formulas (7), (10), (16), (23) and the individual isomers embraced by Formulas (31) and (32) to base used are chosen to provide the ratio desired for any particular salt. For preparing, for example, the calcium salts or magnesium salts, the free acid starting material can be treated with at least one half molar equivalent of pharmaceutically acceptable base to yield a neutral salt. When the aluminum salts are prepared, at least one third molar equivalent of the pharmaceutically acceptable base are employed if a neutral salt product is desired.

In the preferred procedure, the calcium salts and magnesium salts of the prostatrienoic acid compounds hereof can be prepared by treating the corresponding sodium or potassium salts with at least 0.5 molar equivalent of calcium chloride or magnesium chloride, respectively, in an aqueous solution, alone or in combination with an inert water-miscible organic solvent, at a temperature of from about 20° to about 100° C. Preferably, the aluminum salts of the prostadienoic acids of the present invention can be prepared by treating the corresponding free acids with at least one third molar equivalent of an aluminum alkoxide, such as aluminum triethoxide, aluminum tripropoxide and the like, in a hydrocarbon solvent, such as benzene, xylene, cyclohexane and the like, at a temperature of from 20° to about 115° C. Similar procedures can be used to prepare salts of inorganic bases which are not sufficiently soluble for easy reaction.

The salt products are isolated by conventional methods.

The compounds of the present invention exhibit prostaglandin-like biological activities and thus are useful in the treatment of mammals where the use of prostaglandins is indicated.

Particularly, these compounds have luteolytic activity and thus are useful for controlling the reproductive cycle in female mammals and for inducing estrus and regulating ovulation in female animals such as horse, cow and swine. They are also useful for inducing labor in pregnancy and for inducing menses in humans to correct or reduce menstrual abnormalities.

The compounds of the present invention are also bronchodilators and thus are useful in treating mammals for bronchial spasm or wherever bronchodilators are indicated. They are also useful in controlling or palliating hypertension in mammals and further exhibit central nervous system depressant activity in mammals, and are useful as sedatives.

The present compounds can be administered in a wide variety of dosage forms, either alone or in combination with other pharmaceutically compatible medicaments, in the form of pharmaceutical compositions suited for oral or parenteral administration or inhalation in the case of bronchodilators. Intravaginal and intrauterine are alternative routes of administration. They are typically administered as pharmaceutical compositions consisting essentially of the free acid, salt or ester of the invention and a pharmaceutical carrier. The pharmaceutical carrier can be either a solid material, liquid or aerosol, in which the compound (free acid, salt or ester) is dissolved, dispersed or suspended, and can optionally contain small amounts of preservatives and/or pH buffering agents. Suitable preservatives which can be used include, for example, benzyl alcohol and the like. Suitable buffering agents include, for example, sodium acetate and pharmaceutical phosphate salts and the like.

The liquid compositions can, for example, be in the form of solutions, emulsions, suspensions, syrups, or elixirs. The solid compositions can take the form of tablets, powders, capsules, pills or the like, preferably in unite dosage forms for simple administration or precise dosages. Suitable solid carriers include, for example, pharmaceutical grades of starch, lactose, sodium saccharin, talcum, sodium bisulfite and the like.

For inhalation administration, the free acids, salts and esters can, for example, be administered as an aerosol comprising the compounds or salts in an inert propelant together with a cosolvent, e.g., ethanol, together with optional preservatives and buffering agents. Additional general information concerning the inhalation administration of aerosols can be had by reference to U.S. Pat. Nos. 2,868,691 and 3,095,355.

The compounds of this invention are typically administered in dosages of from about 0.1 to about 100 $\mu$g. per Kg. of body weight. The precise effective dosage will, of course, vary depending upon the mode of administration, condition being treated and host.

The following examples illustrate the invention, but are not intended to limit its scope. All mixture ratios used with regard to liquids refer to volume ratios. The term room temperature means a temperature of from about 20° to about 27° C. By the term "Florisil" is meant commercially available magnesium silicate used in chromatography. Also where necessary, the preparation and examples are repeated to provide sufficient starting material for subsequent examples.

PREPARATION 1

1.8 G. of dl-9-oxo-11α,15α-dihydroxyprosta-5-cis,13-trans-dienoic acid are dissolved in 54.0 ml. of glacial acetic acid, and then 6.0 ml. of water is added to this solution. The mixture is then heated at 60° C. under nitrogen for 18 hours. The solvent is then removed under vacuum at 55° C. and the residue is dissolved in ethyl acetate:cyclohexane (20:80), together with methylene chloride, and applied to a column of 180 g. of acid-washed silica gel. Elution is effected with increasing percentages of ethyl acetate in cyclohexane and finally with ethyl acetate. The first fractions obtained from the column contain dl-9-oxo-15α-acetoxyprosta-5-cis,10,13-trans-trienoic acid. The intermediate fractions contain a mixture of dl-9-oxo-15α-acetoxyprosta-5-cis,10,13-trans-trienoic acid and dl-9-oxo-15α-hydroxyprosta-5-cis,10,13-trans-trienoic acid. The terminal fraction contain dl-9-oxo-15α-hydroxyprosta-5-cis,10,13-trans-trienoic acid. The terminal fractions which are homogeneous (as determined by thin layer chromatography) are combined and the solvent evaporated under vacuum to yield a residue of dl-9-oxo-15α-hydroxyprosta-5-cis,10,13-trans-trienoic acid, which is dissolved in 15 ml. of absolute methanol and cooled to −25° C. To this cooled solution is added a pre-cooled solution, dropwise during one hour, of 10.2 ml. of 30% hydrogen peroxide and 3.2 ml. of 25% potassium hydroxide, whilst maintaining the reaction temperature within the range of −10 to −15° C., and then maintaining the temperature at −20° C. for 2 additional hours. 1.0 Ml. of glacial acetic acid is then added at −15° to 20° C to a pH range of 4.5 to 5.5 and the cold reaction mixture is then extracted with three equal volumes of methylene chloride. The combined organic phases are washed with water, saturated sodium chloride solution, dried over sodium sulfate, and the solvent removed under vacuum, at a temperature of 35° C., to yield a residue of dl-9-oxo-10ξ11ξ-epoxy-15α-hydroxyprosta-5-cis,13-transdienoic acid which is dissolved in 18.0 ml. of dimethoxyethane (distilled from sodium) and 2.5 ml. of water is added, followed by 2.25 g. of aluminum amalgam (see Reagents for Organic Synthesis, Fieser and Fieser, Vol. 1, John Wiley and Sons, Inc., 1967). The reaction mixture is vacuum purged with nitrogen and vigorously stirred at room temperature for eight hours. Progress of the reaction is followed by the disappearance of dl-9-oxo-10ξ11ξ-epoxy-15α-hydroxyprosta-5-cis,13-trans-dienoic acid, by thin layer chromatography. 18.0 Ml. of methylene chloride are added, followed by cooling (to 0° to 5° C.), and the addition of a cooled (0° to 5° C.) solution of 1.65 ml. of concentrated hydrochloric acid (22° Be) and 10.2 ml. of water, with stirring. The organic phase is separated and the aqueous phase is extracted with 30 ml. of methylene chloride. The aqueous phase is filtered through Celite (diatomacious earth) and extracted twice with methylene chloride (45 ml.). The combined organic extracts are washed with water until neutral, dried over anhydrous sodium sulfate, and the solvents are removed under vacuum to yield a residue of dl-9-oxo-11α,15α-dihydroxyprosta-5-cis,13-trans-dienoic acid and dl-9-oxo-11β,15α-dihydroxyprosta-5-cis,13-trans-dienoic acid. The 11β-hydroxy isomer (less polar) is separated from the 11α-hydroxy isomer (more polar) by column chromatography using silica gel (1:100/wt:wt/prostaglandin:silica gel) and gradient elution with ethyl acetate:hexane:formic acid (25:75:1 to 90:10:1).

The earlier fractions containing the less polar 11β-hydroxy compound and exhibiting one homogeneous spot by thin layer chromatography (ethyl acetate:hexane:formic acid:70:30:2, Rf ca. 0.3) are combined and evaporated under vacuum to yield a residue of dl-9-oxo-11β,15α-dihydroxyprosta-5-cis,13trans-dienoic acid, which is dissolved in 40 ml. of methylene chloride and 4.0 ml. of methanol. An excess of ethereal diazomethane is added and the reaction mixture is allowed to stand for 15 minutes and then evaporated to yield a residue of the methyl ester of dl-9-oxo-11β,15α-dihydroxyprosta5-cis,13-trans-dienoic acid (11), which is further purified by column chromatography on silica gel, eluting with ethyl acetate:hexane (30:70).

EXAMPLE 1

To a solution of 2.4 g. of the methyl ester of 8R-9-oxo-11α,15α-dihydroxyprosta-5-cis,13-trans-dienoic acid (1), see U.S. Pat. No. 3,772,350, in 19.2 ml. of dichloromethane (previously dried over phosphorous pentoxide) there is added 1.7 ml. of dihydropyran and 16.6 mg. of p-toluenesulfonic acid. After a 10 minute reaction period, at room temperature, ten drops of pyridine is added, the reaction mixture is extracted with ether, washed with saturated sodium chloride solution (2 × 23 ml.), dried, filtered and evaporated to yield 3.1 g. of the methyl ester of 8R-9-oxo-11α,15α-bis-(tetrahydropyran-2-yloxy)prosta-5-cis,13-trans-dienoic acid (2), an oil, having an $[\alpha]_D^{CHCl_3}$ −69.01° (2.0 mg./1 ml.); IR: $\nu_{max.}^{CHCl_3}$ 1741, 971 cm.$^{-1}$; NMR: $\delta_{TMS}^{CDCl_3}$ 0.87 (t, 3H), 2.83 (t,2H), 3.28–4.14 (m, 6H), 3.66 (s, 3H), 4.68 (m, 2H), 5.34–5.76 (m, 4H).

Similarly, substituting the methyl ester of dl-9-oxo-11α,15α-dihydroxyprosta-5-cis,13-trans-dienoic for the corresponding 8R compound is productive of the methyl ester of dl-9-oxo-11α,15α-bis-(tetrahydropyran-2-yloxy)-prosta-5-cis,13-trans-dienoic acid.

EXAMPLE 2

To a solution of 3.1 g. of the methyl ester of 8R-9-oxo-11α,15α-bis-(tetrahydropyran-2-yloxy)-prosta-5-cis, 13-trans-dienoic acid (2) in 62 ml. of methanol at −18° C. there is added a cooled solution of 3.1 g. of sodium borohydride in 4.5 ml. of water and 31 ml. of methanol. After 20 minutes at −18° C., there is added 31. ml. of acetic acid in 52 ml. of water. The reaction mixture is extracted with dichloromethane, washed to neutral pH with a saturated sodium chloride solution, dried, filtered, evaporated and chromatographed on silica gel plates, using hexane:ethyl acetate (64:36) as the eluting solvent, to yield 1.352 g. of the methyl ester of 8R-9α-hydroxy-11α,15α-bis-(tetrahydropyran-2-yloxy)-prosta-5-cis,13-trans-dienoic acid (3), an oil, having an $[\alpha]_D^{CHCl_3}$ +9.8° (3.28 mg./1 ml.); IR: $\nu_{max.}^{CHCl_3}$ 3515, 1731, 979 cm.$^{-1}$; NMR: $\delta_{TMS}^{CDCl_3}$ 0.88 (t, 3H), 2.30 (t, 2H), 3.32–420 (m, 7H), 3.65 (s, 3H), 4.65 (m, 2H), 5.23–5.63 (m, 4H); and 1.105 g. of the methyl ester of 8R-9β-hydroxy-11α,15α-bis-(tetrahydropyran-2-yloxy)-prosta-5-cis,13-trans-dienoic acid (4), and oil, having an $[\alpha]_D^{CHCl_3}$ −22.68° (2.69 mg./1 ml.); IR: $\nu_{max.}^{CHCl_3}$ 3600, 3485, 1730, 980 cm.$^{-1}$; NMR: $\delta_{TMS}^{CDCl_3}$ 0.87 (t, 3H), 2.30 (t, 2H), 3.26–4.12 (m, 7H), 3.64 (s, 3H), 4.43 (m, 2H), 5.26–5.60 (m, 4H).

Similarly substituting the methyl ester of dl-9-oxo-11α,15α-bis-(tetrahydropyran-2-yloxy)-prosta-5-cis,13-trans-dienoic acid for the corresponding 8R compound is productive of the methyl ester of dl-9α- hydroxy-11α,15αbis-(tetrahydropyran-2-yloxy)-prosta-5-cis,13-trans-dienoic acid and the methyl ester of dl-9β-hydroxy-11α,15α-bis(tetrahydropyran-2-yloxy)-prosta-5-cis,13-trans-dienoic acid.

An alternative procedure for the preparation of the methyl ester of 8R-9α-hydroxy-11α,15α-bis-(tetrahydropyran-2-yloxy)-prosta-5-cis,13-trans-dienoic acid (3) is as follows:

In a three-neck round bottomed flask containing a magnetic stirring bar and equipped with an addition funnel and a gas inlet tube for argon, there is placed 36 mg. of dry potassium chloride, 2.5 ml. of anhydrous tetrahydrofuran, and 0.5 ml. of a 1M solution of lithium tri-sec-butylborohydride (Lithium Selectride) in tetrahydrofuran. The resultant mixture is cooled to −73° C. and a solution of 215 mg. of the methyl ester of 8R-9-oxo-11α,15α-bis-(tetrahydropyran2-yloxy)-prosta-5-cis,13-trans-dienoic acid (2) in 2.5 ml. of anhydrous tetrahydrofuran is added dropwise slowly with stirring. The reaction is followed by thin layer chromatography [silica gel/hexane:ethyl acetate (60:40)] and is complete after ten minutes. Stirring at this temperature is however, continued for an additional thirty minutes. There is then added, at the same temperature, 0.25 ml. of 3M sodium hydroxide solution and 0.25 ml. of 30% hydrogen peroxide. After fifteen minutes, the product is extracted into cold ethyl acetate, the extract is washed to neutrality with water, and then dried over magnesium sulfate. The solvent is removed under vacuum to give 285 mg. of a crude product which is chromatographed on a column of Florisil (20 g.) eluting with hexane:ethyl acetate (95:5) to obtain 170 mg. of the methyl ester of 8R-9α-hydroxy-11α,15α-bis-(tetrahydropyran-2-yloxy)-prosta-5-cis,13-trans-dienoic acid (3), having the physical constants set forth above.

Similarly, substituting the methyl ester of dl 9-oxo1-1α,15α-bis-(tetrahydropyran-2-yloxy)-prosta-5-cis,13-transdienoic acid for the corresponding 8R compound, in the alternative procedure, is productive of the methyl ester of dl 9α-hydroxy-11α,15α-bis-(tetrahydropyran-2-yloxy)-prosta-5-cis, 13-trans-dienoic acid.

EXAMPLE 3

Method A. 0.623 G. of the methyl ester of 8R-9α-hydroxy-11α,15α-bis-(tetrahydropyran-2-yloxy)-prosta-5-cis, 13-trans-dienoic acid (3) is submitted to three azeotropic distillations from sodium dried toluene and then is dissolved in 18 ml. of dichloromethane (previously dried over phosphorus pentoxide). The temperature is lowered to −10° to −15° C. 0.410 G. of N(2-chloro-1,1,2-trifluoroethyl)diethylamine is added and the reaction is kept at this temperature for 4 hours. The reaction mixture is added to a saturated sodium bicarbonate solution, the product is extracted with dichloromethane, the extract is washed with a saturated sodium chloride solution to neutral pH, dried, filtered, evaporated and chromatographed over a column of Florisil (50 g.) eluting with hexane:ether (40:60) to yield 0.425 g. of a mixture containing the methyl ester of 8R-9β-fluoro-11α,15α-bis-(tetrahydropyran-2-yloxy)-prosta-5-cis,13-trans-dienoic acid (5).

Method B. 1.603 G. of the methyl ester of 9α-hydroxy-11α,15α-bis-(tetrahydropyran-2-yloxy)-prosta-5-cis-13-transdienoic acid (3) is submitted to three azeotropic distillations from sodium dried toluene and is then dissolved in 25 ml. of anhydrous dichloromethane. The temperature of the mixture is lowered to −10° to −15° C. and there is added 1.11 g. of N(2-chloro-1,1,2-trifluoroethyl)diethylamine. The reaction mixture is maintained at −10° to −15° C. for 3.45 hours and then poured into a saturated sodium bicarbonate solution. The product is extracted with dichloromethane, washed with a saturated salt solution to neutral pH, filtered and evaporated. The thus obtained 2.7 g. of crude product is then treated with 15 ml. of methanol and 180 mg. of potassium carbonate at 0° C. for 2 hours, followed by neutralization with acetic acid, extraction with dichloromethane, evaporation under vacuum and purification by column chromatography on Florisil (150 g.), eluting with hexane:ether (80:20), to give 156 mg. of the methyl ester of 8R-9β-fluoro-11α,15α-bis-(tetrahydropyran-2-yloxy)-prosta-5-cis,13-trans-dienoic acid (5), an oil having an $[\alpha]_D^{CHCl_3}$ −10.45° (3.35 mg./1 ml.) IR: $\nu_{max.}^{CHCl_3}$ 1738, 977 cm.$^{-1}$; NMR $\delta_{TMS}^{CDCl_3}$ 0.85 (m, 3H), 2.26 (t, 2H), 3.20–4.23 (m, 6H), 4.58 (m, 2.5H), 5.00–5.65 (M, 4.5H).

Similarly substituting the methyl ester of dl-9α-hydroxy-11α,15α-bis-(tetrahydropyran-2-yloxy)-prosta-5-cis, 13-trans-dienoic acid for the corresponding 8R compound, in Method A or B, is productive of the methyl ester of dl9β-fluoro-11α,15α-bis-(tetrahydropyran-2-yloxy)-prosta-5-cis,13-trans-dienoic acid.

EXAMPLE 4

0.486 G. of the methyl ester of 8R-9β-fluoro-11α,15α-bis-(tetrahydropyran-2-yloxy)-prosta-5-cis,13-trans-dienoic acid (5) is dissolved in 11.1 ml. of acetic acid:water (65:35) and maintained at room temperature for 8.30 hours. The solvent is evaporated at reduced pressure and the residue is purified by thin layer chromatography on silica gel, eluting with ethyl acetate:hexane (95:5), followed by extraction from the plate with acetone to give 0.218 g. of the methyl ester of 8R-9β-fluoro-11α,15α-dihydroxyprosta-5-cis, 13-trans-dienoic acid (6), an oil, having an $[\alpha]_D^{CHCl_3}$ +9.5° (3.46 mg./1 ml.); IR: $\nu_{max.}^{CHCl_3}$ 3620, 1738, 973 cm.$^{-1}$; $^{19}$F NMR: $\delta_{TMS}^{CDCl_3}$ 165.2 (m, 1F); NMR: $\delta_{TMS}^{CDCl_3}$ 0.88 (t, 3H), 2.29 (t, 2H), 3.65 (s, 3H), 4.06 (m, 2H), 3.45, 4.99 (multiplets, 1H), 5.30–5.57 (m, 4H); MS (as bis-trimethylsilyl ether): m/e 443 (M$^+$−C$_5$H$_{11}$).

Similarly, substituting the methyl ester of dl-9β-fluoro-11α,15α-bis-(tetrahydropyran-2-yloxy)-prosta-5-cis, 13-trans-dienoic acid for the corresponding 8R compound is productive of the methyl ester of dl-9β-fluoro-11α, 15α-dihydroxyprosta-5-cis,13-trans-dienoic acid.

EXAMPLE 5

To a solution of 3.4 ml. of methanol and 0.215 g. of the methyl ester of 8R-9α-fluoro-11α,15α-dihydroxyprosta-5-cis,13-trans-dienoic acid (6) water is added until turbidity develops. The thus obtained mixture is then warmed on a steam-bath between 40° and 48° C., 0.182 g. of anhydrous potassium carbonate is added, the temperature is maintained at 40°–48° C. for one hour and then left at room temperature for 72 hours. The reaction mixture is evaporated to one half of its original volume, made acidic with a saturated solution of oxalic acid to about pH 2, and extracted four times with ethyl acetate (168 ml.). The extract is washed twice with a saturated solution of sodium potassium tartrate (10.7 ml.) dried, filtered, evaporated, and purified by thin layer chromatography on silica gel, eluting with chloroform:methanol (95:5). The crude product is extracted with methanol and evaporated to dryness. A solution of 9.8 ml. of water and 24 drops of acetic acid is then added, followed by five extractions with ethyl acetate:ether (1:1, 9.8 ml.). The thus obtained extracts are combined, washed with 4.9 ml. of water and 4.9 ml. of saturated sodium chloride solution, dried, filtered and evaporated to yield 0.1734 g. of 8R-9β-fluoro-11α,15α-dihydroxyprosta-5-cis,13-trans-dienoic acid (7), an oil, having an $[\alpha]_D^{CHCl_3}$ +9.3° (3.0 mg./1 ml.); IR: $\nu_{max.}^{CHCl_3}$ 3610, 3410, 2665, 1715, 972 cm.$^{-1}$; NMR: $\delta_{TMS}^{CDCl_3}$ 0.87 (t, 3H), 2.32 (t, 2H), 4.06 (m, 2H), 4.50, 5.04 (multiplets, 1H), 5.23 (m, 3H), 5.36–5.60 (m, 4H); $^{13}$C NMR: $\delta_{TMS}^{CDCl_3}$ 73.179 (C-15), 75.162 (C-11), 96.439 (C-9), 127.632 (C-6), 130.753 (C-5), 132.638 (C-13), 135.987 (C-14), 177.567 (C-1).

Similarly, substituting the methyl ester of dl-9β-fluoro-11α,15α-dihydroxyprosta-5-cis,13-trans-dienoic acid for the corresponding 8R compound is productive of dl-9β-fluoro-11α,15α-dihydroxyprosta-5-cis,13-trans-dienoic acid.

EXAMPLE 6

Method A. Six hundred and twenty milligrams of the methylester of 8R-9β-hydroxy-11α,15α-bis-(tetrahydropyran-2-yloxy)-prosta-5-cis,13-trans-dienoic acid (4) is submitted to three azeotropic distillations with toluene (which had previously been dried over sodium) and then is dissolved in 19 ml. of dichloromethane (previously dried over phosphorous pentoxide). The temperature of the solution is lowered to −10 to −15° C. and 0.409 g. of N(2-chloro-1,1,2-trifluoroethyl)diethylamine is added. After a reaction time of 3.45 hours at −10° to −15° C. the solution is poured into a saturated sodium bicarbonate solution, extracted with methylene chloride, the extract washed with saturated sodium chloride solution to neutral pH, dried, filtered, evaporated, and purified by column chromatography over Florisil (60 g.), eluting with hexane:ether (90:10), to obtain 0.398 g. of the methyl ester of 8R-9α-fluoro-11α, 15α-bis-(tetrahydropyran-2-yloxy)-prosta-5-cis,13-trans-dienoic acid (8), an oil, having the physical constants set forth below in Method B.

Method B. 0.2 G. of the methyl ester of 8R-9β-hydroxy-11α,15α-bis-(tetrahydropyran-2-yloxy)-prosta-5-cis,13-transdienoic acid (4) is submitted to three azeotropic distillations from toluene (previously dried over sodium) and then dissolved in 8.7 ml. of dichloromethane (previously dried over phosphorous pentoxide). The temperature is lowered to −10° to −15° and 0.120 g. of N(2-chloro-1,1,2-trifluoroethyl)diethylamine is added, and the reaction mixture is maintained at this temperature for 3.30 hours, after which it is poured into a saturated sodium bicarbonate solution, extracted with dichloromethane, the extract washed with saturated sodium chloride solution to neutral pH, dried, filtered, evaporated, and purified by column chromatography over Florisil, eluting with hexane:ether (90:10), to give 0.098 g. of a mixture which is treated with 20 mg. of anhydrous granular potassium carbonate, using 0.3 ml. of methanol as a solvent, at 0° C. for 2.15 hours. The reaction mixture is neutralized with acetic acid and the product extracted with dichloromethane. Evaporation of the solvent and purification of the residue by column chromatography on Florisil (20 g.) using hexane-ether (70:30) affords 0.067 g. of the methyl ester of 8R-9α-fluoro-11α,15α-bis-(tetrahydropyran-2-yloxy)-prosta-5-cis,13-trans-dienoic acid (8), an oil, having an $[\alpha]_D^{CHCl_3}$ −55.99° (2.84 mg./1 ml.), IR: $\nu_{max.}^{CHCl_3}$ 1728, 976 cm.$^{-1}$; NMR; $\delta_{TMS}^{CDCl_3}$ 0.87 (m, 3H), 2.28 (t, 2H), 3.26–4.09 (m, 6H), 3.61 (s, 3H), 4.40, 5.20 (multiplets, 1H), 4,62 (m, 2H), 5.22–5.60 (m, 4H).

Similarly, substituting the methyl ester of dl-9β-hydroxy-11α,15α-bis-(tetrahydropyran-2-yloxy)-prosta-5-cis,13-trans-dienoic acid for the corresponding 8R compound is productive of the methyl ester of dl-9α-fluoro-11α,15α-bis-(tetrahydropyran-2-yloxy)-prosta-5-cis,13-trans-dienoic acid.

EXAMPLE 7

Seven hundred and sixty milligrams of the methyl ester of 8R-9α-fluoro-11α,15α-bis-(tetrahydropyran-2-yloxy)-prosta-5-cis,13-trans-dienoic (8) in 17.5 ml. of a solution of acetic acid:water (65:35) is allowed to stand at room temperature for seven hours. The solvent is evaporated at reduced pressure and the residue is purified by thin layer chromatography, using ethyl acetate:-hexane (86:14) as the eluting solvent, to yield 0.286 g. of the methyl ester of 8R-9α-fluoro-11α,15α-dihydroxyprosta-5-cis,13,trans-dienoic acid (9), an oil having an $[\alpha]_D^{CHCl_3}$ +28.52° (2.56 mg./1 ml.); IR: $\nu_{max.}^{CHCl_3}$ 3620, 3425, 1735, 971 cm.$^{-1}$ NMR: $\delta_{TMS}^{CDCl_3}$ 0.88 (t, 3H), 2.29 (t, 2H), 3.65 (s, 3H), 3.75–4.15 (m, 2H), 4.62, 5.14 (multiplets, 1H), 5.28–5.60 (m, 3H), 5.63 (q, 1H); $^{19}$F NMR: $\delta_{TMS}^{CDCl_3\ CFCl}$ 183.2 (m, F), MS (as bis-trimethylsilyl ether): m/e 514 (M$^+$), 494 (M$^+$–HF), 443 (M$^+$–C$_5$H$_{11}$), 423 (443-HF), 373 (M$^+$-C$_6$H$_{10}$CO$_2$CH$_3$).

Similarly, substituting the methyl ester of dl-9α-fluoro-11α,15α-bis-(tetrahydropyran)-2-yloxy)-prosta-5-cis,13-trans-dienoic acid for the corresponding 8R compound is productive of the methyl ester of dl-9α-fluoro-11α,15α-dihydroxyprosta-5-cis,13-trans-dienoic acid.

EXAMPLE 8

To a solution of 0.266 g. of the methyl ester of 8R-9α-fluoro-11α,15α-dihydroxyprosta-5-cis,13-trans-dienoic acid (9) in 4.15 ml. of methanol water is added until turbidity develops. The mixture is placed on a water-bath at 40–45° C. and 0.221 g. of anhydrous potassium carbonate is added. After one hour at the above temperature and 72 hours at room temperature, the reaction mixture is evaporated to about one half its original volume, acidified to about pH 2 with a saturated oxalic acid solution, extracted four times with ethyl acetate (194 ml.), washed twice with a saturated solution of sodium potassium tartrate, dried, filtered, and evaporated. The residue is subjected to thin layer chromatography on silica gel, eluting with chloroform-:methanol (95:5), and the product is extracted from the plate with methanol (384 ml.) and evaporated to dryness. To the thus obtained residue 10.2 ml. of water, containing 25 drops of acetic acid, is added, followed by five extractions with ethyl acetate:ether (1:1, 10.2 ml.). The extracts are combined, washed with 5.1 ml. of water and 5.1 ml. of saturated sodium chloride solution, dried over magnesium sulfate, filtered and evaporated to yield 0.224 g. of 8R-9α-fluoro-11α,15α-dihydroxyprosta-5-cis,13-trans-dienoic acid (10), having a melting point of 48° to 49.5° C; Anal. Calcd. for C$_{20}$H$_{33}$O$_4$F: C, 67.39; H, 9.33; F, 5.33; Found: C, 67.67; H, 9.46; F, 5.19.

Similarly, substituting the methyl ester of dl-9α-fluoro-11α,15α-dihydroxyprosta-5-cis,13-trans-dienoic acid for the corresponding 8R compound is productive of dl-9α-fluoro-11α,15α-dihydroxyprosta-5-cis,13-trans-dienoic acid.

EXAMPLE 9

To a solution of 3.6 g. of the methyl ester of 8R-9-oxo-11β,15α-dihydroxyprosta-5-cis,13-trans-dienoic acid (11), see U.S. Pat. No. 3,772,350, in 25 ml. of dichloromethane (previously dried over phosphorous pentoxide) there is added 2.65 ml. of dihydropyran and 25 mg. of p-toluenesulfonic acid. After 10 minutes at room temperature fifteen drops of pyridine is added, followed by extraction of the product with ether. The ether extract is washed with saturated sodium chloride solution (2 × 34ml.), dried, filtered and evaporated to yield 4.68 g. of the methyl ester of 8R-9-oxo-11β,15α-bis-(tetrahydropyran-2-yloxy)-prosta-5-cis,13-trans-dienoic acid (12), an oil, having an $[\alpha]_D^{CHCl_3}$ −40.06° (2.79 mg./1 ml); IR: $\nu_{max.}^{CHCl_3}$ 1740, 977 cm$^{-1}$; NMR: $\delta_{TMS}^{CDCl_3}$ 0.90 (t, 3H), 2.25 (t, 2H), 3.30–4.12 (m, 6H), 3.50 (s, 3H), 4.72 (m, 2H), 5.23–5.53 (m, 2H), 5.64–5.80 (m, 2H).

Similarly, substituting the methyl ester of dl-9-oxo-11β,15α-dihydroxyprosta-5-cis,13-trans-dienoic acid for the corresponding 8R compound is productive of the methyl ester of dl-9-oxo-11β,15α-bis-(tetrahydropyran-2-yloxy)-prosta-5-cis, 13-trans-dienoic acid.

EXAMPLE 10

To a solution of 4.8 g. of the methyl ester of 8R-9-oxo-11β,15α-bis-(tetrahydropyran-2-yloxy)-prosta-5-cis,13-trans-dienoic acid (12) in 96 ml. of methanol at −18° C. there is added a cooled solution of 4.8 g. of sodium borohydride in 6.95 ml. of water and 48.3 of methanol. After a period of 25 minutes, there is added a solution of 4.8 ml. of acetic acid in 80 ml. of water, and the mixture is extracted with dichloromethane, and then washed with a saturated sodium chloride solution to neutral pH, followed by evaporation of the solvent and chromatography on a column of Florisil (125 g.), eluting with dichloromethane:ether (85:15), to yield 4.0 g. of the methyl ester of 8R-9β-hydroxy-11β,15α-bis-(tetrahydropyran-2-yloxy)-prosta-5-cis,13-trans-dienoic acid (13), an oil, having an $[\alpha]_D^{CHCl_3}$+23.13° (3.2 mg./1 ml.); IR: $\nu_{max.}^{CHCl_3}$ 3545, 1734, 979 cm.$^{-1}$; NMR: $\delta_{TMS}^{CDCl_3}$ 0.89 (t, 3H), 2.33 (t, 2H), 3.27–4.28 (m, 6H), 3.66 (s, 3H), 4.70 (m, 2H), 5.10–5.93 (m, 4H).

Similarly, substituting the methyl ester of dl-9-oxo-11β,15α-bis-(tetrahydropyran-2-yloxy)-prosta-5-cis,13-trans-dienoic acid for the corresponding 8R compound is productive of the methyl ester of dl-9β-hydroxy-11β,15α-bis-(tetrahydropyran-2-yloxy)-prosta-5-cis,13-trans-dienoic acid.

EXAMPLE 11

Thirty-three hundred milligrams of the methyl ester of 8R-9β-hydroxy-11β,15α-bis-(tetrahydropyran-2-yloxy)-prosta- 5-cis, 13-trans-dienoic acid (13) is submitted to three azeotropic distillations with sodium dried toluene, and then dissolved in 50 ml. of dry dichloromethane. The temperature is lowered to −10° to −15° C., and 2.1 g. of N(2-chloro-1,1,2-trifluoroethyl)-diethylamine is added. The reaction is maintained at the above temperature for 4.3 hours and then poured into 125 ml. of a saturated sodium bicarbonate solution. The product is extracted with dichloromethane, washed with a saturated sodium chloride solution to neutrality, dried, filtered and evaporated to yield 5.1 g. of a crude residue which is taken up in 25 ml. of methanol containing 260 ml. of anhydrous granular potassium carbonate and kept at 0° C. for 2.5 hours, followed by neutralization with acetic acid, extraction with dichloromethane, evaporation under vacuum and purification by thin layer chromatography on silica gel, eluting with hexane:ether (70:30), to yield 1.150 g. of the methyl ester of 8R-9α-fluoro-11β,15α-bis-(tetrahydropyran-2-yloxy)-prosta-5-cis,13-trans-dienoic acid (14).

Similarly, substituting the methyl ester of dl-9β-hydroxy-11β,15α-bis-(tetrahydropyran-2-yloxy)-prosta-5-cis,13-trans-dienoic acid for the corresponding 8R compound is productive of the methyl ester of dl-9α-fluoro-11β,15α-bis-(tetrahydropyran-2-yloxy)-prosta-5-cis,13-trans-dienoic acid.

EXAMPLE 12

Seven hundred milligrams of the methyl ester of 8R-9α-fluoro-11β,15α-bis-(tetrahydropyran-2-yloxy)-prosta-5-cis,13-trans-dienoic acid (14) is dissolved in 15 ml. of a solution of acetic acid:water (65:35), and the reaction solution is stirred at room temperature for 8 hours. The solvent is removed under reduced pressure, and the product is purified by thin layer chromatography, using ether as the eluting solvent, to yield 300 mg. of the methyl ester of 8R-9α-fluoro-11β,15α-dihydroxyprosta-5-cis,13-trans-dienoic acid (15), an oil, having an $[\alpha]_D^{CHCl_3}$+68° (2.7 mg./1 ml.); IR: $\nu_{TMS}^{CHCl_3}$ 3620, 3440, 1732, 975 cm.$^{-1}$; NMR: $\delta_{TMS}^{CDCl_3}$ 0.87 (t, 3H), 2.29 (t, 2H), 3.64 (s, 3H), 4.09 (m, 1H), 4.31 (m, 1H), 4.76–5.26 (multiplets, 1H), 5.30–5.50 (m, 2H), 5.59–5.66 (m, 2); MS (as bis-trimethylsilyl ether) 443 (M$^+$—C$_5$H$_{11}$), 423 (443-HF), 373 (M$^+$—C$_6$H$_{10}$CO$_2$CH$_3$).

Similarly, substituting the methyl ester of dl-9α-fluoro-11β,15α-bis-(tetrahydropyran-2-yloxy)-prosta-5-cis,13-trans-dienoic acid for the corresponding 8R compound is productive of the methyl ester of dl-9α-fluoro-11β,15α-dihydroxyprosta-5-cis,13-trans-dienoic acid.

EXAMPLE 13

Two hundred and fifty milligrams of the methyl ester of 8R-9α-fluoro-11β,15α-dihydroxy-prosta-5-cis,13-trans-dienoic acid (15) is dissolved in 4 ml. of methanol and 221 mg. of anhydrous potassium carbonate is added, and the mixture is agitated at room temperature for 62 hours. The solvent is evaporated to one half of its original volume, acidified with oxalic acid and then extracted with ethyl acetate (3 × 75 ml.). The extracts are combined, washed with saturated sodium potassium tartrate solution (2 × 10 ml.); dried over magnesium sulfate, filtered, evaporated to dryness, and purified by thin layer chromatography using chloroform:methanol (95:5). The product is extracted from the plates with 200 ml. of methanol and the extract is evaporated to dryness. A solution of 10 ml. of water containing 25 drops of acetic acid is added and the mixture is extracted five times with 10 ml. portions of a solution of ethyl acetate:ether (1:1). The organic extracts are combined, washed with 5 ml. of water and then with 5 ml. of a saturated sodium chloride solution, dried over magnesium sulfate, filtered and evaporated to dryness at reduced pressure to yield 190 mg. of 8R-9α-fluoro-11β,15α-dihydroxy-prosta-5-cis,13-trans-dienoic acid (16), an oil, having an $[\alpha]_D^{CHCl_3}$ +75° (3.49 mg./1 ml.); IR: $\nu_{max.}^{CHCl_3}$ 3615, 3405, 2665, 1713, 977 cm.$^{-1}$;

NMR: $\delta_{TMS}^{CDCl_3}$ 0.87 (t, 3H), 2.31 (t, 2H), 4.16 (m, 1H), 4.32 (m, 1H), 4.79, 5.29 (multiplets 1H), 5.29–5.70 (m, 4H); $^{13}$C NMR: $\delta_{TMS}^{CDCl_3}$ 72.529 (C-15), 73.829 (C-11), 94.960 (C-9), 128.445 (C-6), 128.770 (C-13), 129.973 (C-5), 136.800 (C-14), 177.014 (C-1); MS: m/e 338 (M$^+$–H$_2$O), 318 (338-HF), 300 (318-H$_2$O).

Similarly, substituting the methyl ester of dl-9α-fluoro-11β,15α-dihydroxyprosta-5-cis,13-trans-dienoic acid for the corresponding 8R compound is productive of dl-9α-fluoro-11β,15α-dihydroxyprosta-5-cis,13-trans-dienoic acid.

EXAMPLE 14

To a solution of 400 mg. of the methyl ester of 8R-9-oxo-11β,15α-dihydroxyprosta-5-cis,13-trans-dienoic acid (11), see U.S. Pat. No. 3,772,350, in 8.2 ml. of methanol, cooled to −18° C., is added a cooled (−18° C.) solution of 400 mg. of sodium borohydride in 0.7 ml. of water and 1.0 ml. of methanol during a 35 minute period with stirring. A solution of 0.4 ml. of glacial acetic acid and 8.0 ml. of water is added and the reaction mixture is extracted with ethyl acetate. The extract is washed to neutrality with water, dried and the ethyl acetate is removed under vacuum to yield a mixture of the 9α-hydroxy and 9β-hydroxy isomers. Preparative thin layer chromatography [chloroform:methanol (93:7)] yields the methyl ester of 8R-9α,11β,15α-trihydroxyprosta-5-cis,13-trans-dienoic acid (17) (the more polar product) and the corresponding 9β-hydroxy isomer (less polar).

Similarly, substituting the methyl ester of dl-9-oxo-11β-15α-dihydroxyprosta-5-cis,13-trans-dienoic acid for the corresponding 8 R compound is productive of the methyl ester of dl-9α,11β,15α-trihydroxyprosta-5-cis,13-trans-dienoic acid and its corresponding dl-9β-hydroxy isomer.

EXAMPLE 15

To a solution of 100 mg. of the methyl ester of 8R-9α,11β,15α-trihydroxyprosta-5-cis,13-trans-dienoic acid (17) in 2.0 ml. of dry acetone, cooled to −40° C., is added 4 ml. of N-trimethylsilyldiethylamine under an argon atmosphere. The reaction mixture is stirred at −40° C. for 3.5 hours, 3.0 ml. of anhydrous methanol are added and the mixture is then warmed to, and kept at, room temperature for fifteen minutes. The solvents are removed under vacuum at room temperature to yield the methyl ester of 8R-9α-hydroxy-11β,15α-bis-(trimethylsilyloxy)-prosta-5-cis,13-trans-dienoic acid (18).

Similarly, substituting the methyl ester of dl-9α,11β,15α-trihydroxyprosta-5-cis,13-trans-dienoic acid for the corresponding 8R compound is productive of dl-9α-11β,15α-bis-(trimethylsilyloxy)-prosta-5-cis,13-trans-dienoic acid methyl ester.

EXAMPLE 16

To 110 mg. of the methyl ester of 8R-9α-hydroxy-11β,15α-bis-(trimethylsilyloxy)-prosta-5-cis,13-trans-dienoic acid (18) dissolved in two ml. of pyridine there is added 0.2 ml. of acetic anhydride and the reaction mixture is allowed to stand for 1.5 hours at room temperature. 0.2 Ml. of water is added and the solvents are removed under vacuum to yield a residue containing the methyl ester of 8R-9α-acetoxy-11β,15α-bis-(trimethylsilyloxy)-prosta-5-cis,13-trans-dienoic acid which is dissolved in twenty ml. of methanol, 0.5 ml. of glacial acetic acid and five ml. of water. The reaction mixture is stirred at room temperature for fifteen hours, followed by evaporation under reduced pressure (to remove methanol) and the residue is mixed with 40 ml. of saturated sodium chloride solution and then extracted with three portions of ethyl acetate (40 ml., 25 ml., and 15 ml.). The combined extracts are washed with water, and saturated aqueous sodium bicarbonate solution, followed by two portions of saturated sodium chloride solution, dried over anhydrous sodium sulfate and evaporated under reduced pressure to yield the methyl ester of 8R-9α-acetoxy-11β,15α-dihydroxyprosta-5-cis,13-trans-dienoic acid (19), which is further purified by column chromatography, using silica gel, and eluting with hexane:ethyl acetate (60:40).

Similarly, substituting the methyl ester of dl-9α-hydroxy-11β,15α-bis-(trimethylsilyloxy)-prosta-5-cis,13-trans-dienoic acid for the corresponding 8R compound is productive of the methyl ester of dl-9α-acetoxy-11β,15α-dihydroxyprosta-5-cis,13-trans-dienoic acid.

EXAMPLE 17

To a solution of 240 mg. of the methyl ester of 8R-9α-acetoxy-11β,15α-dihydroxyprosta-5-cis,13-trans-dienoic acid (19) in two ml. of dichloromethane (previously dried over phosphorous pentoxide) is added 0.2 ml. of dihydropyran and two mg. of p-toluenesulfonic acid. After a 10 minute reaction period, one drop of pyridine is added, the mixture is extracted with ether, washed with saturated sodium chloride solution (2 × 3 ml.), dried, filtered and evaporated to yield a residue containing the methyl ester of 8R-9α-acetoxy-11β,15α-bis-(tetrahydropyran-2-yloxy)-prosta-5-cis,13-trans-dienoic acid. The thus obtained residue is dissolved in ten ml. of anhydrous methanol cooled to −5° C. and treated with 150 mg. of anhydrous potassium carbonate, under a nitrogen atmosphere. The reaction mixture is stirred for three hours at −5° to 0° C., poured into water and neutralized with 1% dilute oxalic acid and extracted with 50 ml. portions of ethyl acetate. The combined organic extracts are washed with saturated sodium chloride solution, dried over sodium sulfate and evaporated to dryness under vacuum, to yield the methyl ester of 8R-9α-hydroxy-11β,15α-bis-(tetrahydropyran-2-yloxy)-prosta-5-cis,13-trans-dienoic acid (20), which is further purified by chromatographing on a column of Florisil (20 g.), eluting with hexane:ethyl acetate (95:5).

Similarly, substituting the methyl ester of dl-9α-acetoxy-11β,15α-dihydroxyprosta-5-cis,13-trans-dienoic acid for the corresponding 8R compound is productive of the methyl ester of dl-9α-hydroxy-11β,15α-bis-(tetrahydropyran-2-yloxy)-prosta-5-cis,13-trans-dienoic acid.

EXAMPLE 18

Method A. 0.623 G. of the methyl ester of 8R-9α-hydroxy-11β,15α-bis-(tetrahydropyran-2-yloxy)-prosta-5-cis, 13-trans-dienoic acid (20) is submitted to three azeotropic distillations from sodium dried toluene and then is dissolved in 18 ml. of dichloromethane (previously dried over phosphorous pentoxide). The temperature is lowered to −10° to −15° C. 0.410 g. of N(2-chloro-1,1,2-trifluoroethyl)diethylamine is added and the reaction is kept at this temperature for 4 hours. The reaction mixture is added to a saturated sodium bicarbonate solution, the product is extracted with dichloromethane, the extract is washed with a saturated sodium chloride solution to neutral pH, dried, filtered, evaporated and chromatographed over a column of Florisil (60 g.) eluting with hexane:ether (40:60) to yield 0.425 g. of a mixture containing the methyl ester of 8R-9β-fluoro-11β,15α-bis-(tetrahydropyran-2-yloxy)-prosta-5-cis,13-trans-dienoic acid (21).

Method B. 1.603 G. of the methyl ester of 8R-9α-hydroxy-11β,15α-bis-(tetrahydropyran-2-yloxy)-prosta-5-cis, 13-trans-dienoic acid (20) is submitted to three azeotropic distillations from sodium dried toluene and is then dissolved in 25 ml. of anhydrous dichloromethane. The temperature of the mixture is lowered to −10° to −15° C. and there is added 1.11 g. of N(2-chloro-1,1,2-trifluoroethyl)diethylamine. The reaction mixture is maintained at −10° to −15° C. for 3.45 hours and then poured into a saturated sodium bicarbonate solution. The product is extracted with dichloromethane, washed with a saturated salt solution to neutral pH, filtered and evaporated. The crude product is then treated with 15 ml. of methanol and 180 mg. of potassium carbonate at 0° C. for two hours, followed by neutralization with acetic acid, extraction with dichloromethane, evaporation under vacuum and purification by column chromatography on Florisil (150 g.), eluting with hexane:ether (80:20), to give the methyl ester of 8R-9β-fluoro-11β,15α-bis-(tetrahydropyran-2-yloxy)-prosta-5-cis,13-trans-dienoic acid (21).

Similarly, substituting the methyl ester of dl-9α-hydroxy-11β,15α-bis-(tetrahydropyran-2-yloxy)-prosta-5-cis, 13-trans-dienoic acid for the corresponding 8R compound, in Method A or B, is productive of the methyl ester of dl-9β-fluoro-11β,15α-bis-(tetrahydropyran-2-yloxy)-prosta-5-cis, 13-trans-dienoic acid.

EXAMPLE 19

0.486 G. of the methyl ester of 8R-9β-fluoro-11β,15α-bis(tetrahydropyran-2-yloxy)-prosta-5-cis,13-transdienoic acid (21) is dissolved in 11.1 ml. of acetic acid:water (65:35) and maintained at room temperature for 8.30 hours. The solvent is evaporated at reduced pressure and the residue is purified by thin layer chromatography on silica gel, eluting with ethyl acetate:hexane (95:5), followed by extraction from the plate with acetone to give 0.218 g. of the methyl ester of 8R-9β-fluoro-11β,15α-dihydroxyprosta-5-cis,13-trans-dienoic acid (22).

Similarly, substituting the methyl ester of dl-9β-fluoro-11β,15α-bis-(tetrahydropyran-2-yloxy)-prosta-5-cis, 13-trans-dienoic acid for the corresponding 8R compound is productive of the methyl ester of dl-9β-fluoro-11β,15α-dihydroxyprosta-5-cis,13-trans-dienoic acid.

EXAMPLE 20

To a solution of 3.4 ml. of methanol and 0.215 g. of the methyl ester of 8R-9β-fluoro-11β,15α-dihydroxyprosta-5-cis,13-trans-dienoic acid (22) water is added until turbidity develops. The thus obtained mixture is then warmed on a steam-bath between 40° and 48° C., 0.182 g. of anhydrous potassium carbonate is added, the temperature is maintained at 40°-48° C. for one hour and then left at room temperature for 72 hours. The reaction mixture is evaporated to one half of its original volume, made acidic with a saturated solution of oxalic acid to about pH 2, and extracted four times with ethyl acetate (168 ml.). The extract is washed twice with a saturated solution of sodium potassium tartrate (10.7 ml.) dried, filtered, evaporated, and purified by thin layer chromatography on silica gel, eluting with chloroform:methanol (95:5). The crude product is extracted with methanol and evaporated to dryness. A solution of 9.8 ml. of water and 24 drops of acetic acid is then added, followed by five extractions with ethyl acetate:ether (1:1, 9.8 ml.). The thus obtained extracts are combined, washed with 4.9 ml. of water and 4.9 ml. of saturated sodium chloride solution, dried, filtered and evaporated to yield 0.1734 g. of 8R-9β-fluoro-11β,15α-dihydroxyprosta-5-cis,13-trans-dienoic acid (23).

Similarly, substituting the methyl ester of dl-9β-fluoro-11β,15α-dihydroxyprosta-5-cis,13-trans-dienoic acid for the corresponding 8R compound is productive of dl-9β-fluoro-11β,15α-dihydroxyprosta-5-cis,13-trans-dienoic acid.

EXAMPLE 21

Seven hundred and forty two milligrams of 2,3-dichloro-5,6-dicyano-1,4-benzoquinone is added to a solution of 371 mg. of the methyl ester of 9β-fluoro-11α,15α-dihydroxyprosta-5-cis,13-trans-dienoic acid [(24; 9β-F, 11α-OH); (15)] in 2.2 ml. of benzene. The reaction mixture is stirred for 18 hours at room temperature and then chromatographed on a column of 160 g. of Florisil, eluting with methylene chloride:ether (90:10) to yield 307 mg. of the methyl ester of 8R-9β-fluoro-11α-hydroxy-15-oxoprosta-5cis,13-transdienoic acid (25; 9β-F, 11α-OH), an oil, having an $[\alpha]_D^{CHCl_3}$ +25° (2.29 mg./1 ml); UV:$\lambda_{max.}^{CH_3OH}$ 229 nm (ε 12,300); IR: $\nu_{max.}^{CHCl_3}$ 3620, 3470, 1733, 1698, 1670, 1629, 972 cm.$^{-1}$; NMR: $\delta_{TMS}^{CDCl_3}$0.88 (m, 3H), 3.47 (s, 3H), 4.27 (m, 1H), 5.40 (m, 2H), 6.10 (d, 1H), 6.72 (q, 1H); MS: m/e 368 (M$^+$), 350 (M$^+$−H$_2$O), 337 (M$^+$−OCH$_3$), 330 (350−HF), 279 (350−C$_5$H$_{11}$), 249 (350−C$_5$H$_{11}$CO), 227 (M$^+$-C$_6$H$_{10}$CO$_2$CH$_3$), 207 (227-HF).

Similarly, substituting the methyl esters of dl-9β-fluoro-11α,15α-dihydroxyprosta-5-cis,13-transdienoic acid, 8R-9α-fluoro-11α,15α-dihydroxyprosta-5-cis,13-transdienoic acid, dl-9α-fluoro-11α,15α-dihydroxyprosta-5-cis,13-transdienoic acid, 8R-9α-fluoro-11β,15α-dihydroxyprosta-5-cis,13-transdienoic acid, dl-9α-fluoro-11β,15α-dihydroxyprosta-5-cis,13-transdienoic acid, 8R-9β-fluoro-11β,15α-dihydroxyprosta-5-cis,13-transdienoic acid, and dl-9β-fluoro-11β,15α-dihydroxyprosta-5-cis,13-transdienoic acid, and for the methyl ester of 8R-9β-fluoro-11α,15α-dihydroxyprosta-5-cis,13-trans-dienoic acid is productive of the methyl esters of dl-9β-fluoro-11α-hydroxy-15-oxoprosta-5-cis,13-transdienoic acid, 8R-9α-fluoro-11α-hydroxy-15-oxoprosta-5-cis,13-transdienoic acid, dl-9α-fluoro-11α-hydroxy-15-oxoprosta-5-cis,13-transdienoic acid, 8R-9α-fluoro-11β-hydroxy-15-oxoprosta-5-cis,13-transdienoic acid, dl-9α-fluoro-11β-hydroxy-15-oxoprosta-5-cis,13-transdienoic acid, 8R-9β-fluoro-11β-hydroxy-15-oxoprosta-5-cis,13-transdienoic acid, and dl-9β-fluoro-11β-hydroxy-15-oxoprosta-5-cis,13-transdienoic acid, respectively.

EXAMPLE 22

To a solution of 232 mg. of the methyl ester of 8R-9β-fluoro-11α-hydroxy-15-oxoprosta-5-cis,13-transdienoic acid (25; 9β-F, 11α-OH) in 1.8 ml. of acetone (distilled from potassium permanganate and calcium carbonate) there is added 4.6 ml. of N-trimethylsilyldiethylamine. The solution is agitated at room temperature under an atmosphere of argon for 1 hour and then evaporated to dryness to yield 260 mg. of the methyl ester of 8R-9β-fluoro-11α-trimethylsilyloxy-15-oxoprosta-5-cis,13-trans-dienoic acid (26; 9β-F, 11α-trimethylsilyloxy).

Similarly substituting the methyl esters of
dl-9β-fluoro-11α-hydroxy-15-oxoprosta-5-cis,13-transdienoic acid,
8R-9α-fluoro-11α-hydroxy-15-oxoprosta-5-cis,13-transdienoic acid,
dl-9α-fluoro-11α-hydroxy-15-oxoprosta-5-cis,13-transdienoic acid,
8R-9α-fluoro-11β-hydroxy-15-oxoprosta-5-cis,13-transdienoic acid,
dl-9α-fluoro-11β-hydroxy-15-oxoprosta-5-cis,13-transdienoic acid,
8R-9β-fluoro-11β-hydroxy-15-oxoprosta-5-cis,13-transdienoic acid, and
dl-9β-fluoro-11β-hydroxy-15-oxoprosta-5-cis,13-transdienoic acid,
for the methyl ester of 8R-9β-fluoro-11α-hydroxy-15-oxoprosta-5-cis,13-trans-dienoic acid is productive of the methyl esters of
dl-9β-fluoro-11α-trimethylsilyloxy-15-oxoprosta-5-cis,13-trans-dienoic acid,
8R-9α-fluoro-11α-trimethylsilyloxy-15-oxoprosta-5-cis,13-trans-dienoic acid,
dl-9α-fluoro-11α-trimethylsilyloxy-15-oxoprosta-5-cis,13-trans-dienoic acid,
8R-9α-fluoro-11β-trimethylsilyloxy-15-oxoprosta-5-cis,13-trans-dienoic acid,
dl-9α-fluoro-11β-trimethylsilyloxy-15-oxoprosta-5-cis,13-trans-dienoic acid,
8R-9β-fluoro-11β-trimethylsilyloxy-15-oxoprosta-5-cis,13-trans-dienoic acid, and
dl-9β-fluoro-11β-trimethylsilyloxy-15-oxoprosta-5-cis,13-trans-dienoic acid, respectively.

EXAMPLE 23

Two hundred and sixty milligrams of the methyl ester of 8R-9β-fluoro-11α-trimethylsilyloxy-15-oxoprosta-5-cis,13-trans-dienoic acid (26; 9β-F, 11α-trimethylsilyloxy) is dissolved in 7.7 ml. of tetrahydrofuran (distilled from lithium aluminum hydride). The temperature is lowered to −40° C. and there is added 0.650 ml. of methylmagnesium bromide (4N) in diethyl ether solution. The reaction mixture is stirred for two hours at −40° C., poured into 20 ml. of saturated aqueous ammonium chloride solution and after stirring several minutes, extracted repeatedly with ethyl acetate, dried, and evaporated to give 268 mg. of a colorless oil,[a mixture of the 9-fluoro-11-trimethylsilyloxy-15β-hydroxy-15α-methyl and 9-fluoro-11-trimethylsilyloxy-15α-hydroxy-15β-methyl compounds of (27) and (28), respectively]. The oil is dissolved in ten ml. of ethanol, six ml. of water is added and the resulting mixture is stirred for 5.30 hours at 25° C. The ethanol is evaporated at reduced pressure and the aqueous residue is diluted with an equal volume of saturated aqueous sodium chloride and then extracted (5 × 25 ml.) with ethyl acetate. The combined extracts are washed with saturated aqueous sodium chloride, dried and evaporated at reduced pressure to give 225 mg. of a mixture of the methyl ester of 8R-9β-fluoro-11α,15β-dihydroxy-15α-methylprosta-5-cis,13-trans-dienoic acid (29; 9β-F, 11α,15β-diOH, 15α-methyl) and the methyl ester of 8R-9β-fluoro-11α,15α-dihydroxy-15β-methylprosta-5-cis,13-trans-dienoic acid (30; 9β-F, 11α,15α-diOH, 15β-methyl).

The above-identified methyl ester mixture is separated by column chromatography on Florisil (20 g.) eluting with methylene chloride:ether (80:20). There is thus obtained 89 mg. of the less polar isomer, the methyl ester of 8R-9β-fluoro-11α,15β-dihydroxy-15α-methylprosta-5-cis,13-transdienoic acid (29; 9β-F, 11α,15β-diOH, 15α-methyl), an oil, having an $[\alpha]_D^{CHCl_3}$ ±0° (3.69 mg./1 ml.); IR: $\nu_{max.}^{CHCl_3}$ 3615, 3445, 1733, 967 cm.$^{-1}$; NMR: $\delta_{TMS}^{CDCl_3}$ 0.87 ($t$, 3H), 1.27 ($s$, 3H), 3.62 ($s$, 3H), 4.03 ($m$, 1H), 4.03 ($m$, 1H), 4.66 ($m$, 1H), 5.30–5.66 (m, 4H); $^{13}$C NMR: $\delta_{TMS}^{CDCl_3}$ 27.926 (15-CH$_3$), 72.89 (C-15), 75.324 (C-11), 94.408 (C-9), 127.437 (C-6), 127.665 (C-13), 130.753 (C-5), 139.8 (C-14), 174.0 (C-1); MS: m/e 457 (M$^+$-C$_5$H$_{11}$), 437 (457-HF), 387 (M$^+$-C$_6$H$_{10}$CO$_2$CH$_3$), 367 (457-TMSOH), and 100 mg. of the more polar isomer, the methyl ester of 8R-9β-fluoro-11α,15α-dihydroxy-15β-methylprosta-5-cis,13-trans-dienoic acid (30; 9α-F, 11α,15α-diOH, 15β-methyl), an oil, having an $[\alpha]_D^{CHCl_3}$ ±0° (2 mg./1 ml.); IR: $\nu_{max.}^{CHCl_3}$ 3610, 3420, 1732, 969 cm.$^{-1}$; NMR: $\delta_{TMS}^{CDCl_3}$ 0.87 ($t$, 3H), 128 ($s$, 3H), 3.62 ($s$, 3H), 4.03 ($m$, 1H), 4.70 ($m$, 1H), 5.18-5.65 (m, 4H); $^{13}$C NMR: $\delta_{TMS}^{CDCl_3}$ 27.893 (15-CH$_3$), 72.854 (C-15), 75.324 (C-11), 96.4 (C-9), 127.469 (C-6), 127.860 (C-13), 130.720 (C-5), 140.603 (C-14), 174.186 (C-1); MS (as bis-trimethylsilyl ether): m/e 457 (M$^+$–C$_5$H$_{11}$), 437 (457-HF), 387 (M$^+$–C$_6$H$_{10}$CO$_2$CH$_3$).

Similarly substituting the methyl esters of
dl-9β-fluoro-11α-trimethylsilyloxy-15-oxoprosta-5-cis,13-trans-dienoic acid,
8R-9α-fluoro-11α-trimethylsilyloxy-15-oxoprosta-5-cis,13-trans-dienoic acid,
dl-9α-fluoro-11α-trimethylsilyloxy-15-oxoprosta-5-cis,13-trans-dienoic acid,
8R-9α-fluoro-11β-trimethylsilyloxy-15-oxoprosta-5-cis,13-trans-dienoic acid,
dl-9α-fluoro-11β-trimethylsilyloxy-15-oxoprosta-5-cis,13-trans-dienoic acid,
8R-9β-fluoro-11β-trimethylsilyloxy-15-oxoprosta-5-cis,13-trans-dienoic acid, and
dl-9β-fluoro-11β-trimethylsilyloxy-15-oxoprosta-5-cis,13-trans-dienoic acid,
for the methyl ester of 8R-9β-fluoro-11α-trimethylsilyloxy-15-oxoprosta-5-cis,13-trans-dienoic acid is productive of the methyl esters of the mixtures of
dl-9β-fluoro-11α,15β-dihydroxy-15α-methyl- and dl-9β-fluoro-11α,15α-dihydroxy-15β-methylprosta-5-cis,13-transdienoic acid,
8R-9α-fluoro-11α,15β-dihydroxy-15α-methyl- and 8R-9α-fluoro-11α,15α-dihydroxy-15β-methylprosta-5-cis,13-transdienoic acid,
dl-9α-fluoro-11α,15β-dihydroxy-15α-methyl- and dl-9α-fluoro-11α,15α-dihydroxy-15β-methylprosta-5-cis,13-transdienoic acid, 8R-9α-fluoro-11β,15β-dihydroxy-15α-methyl- and 8R-9α-fluoro-11β,15α-dihydroxy-15β-methylprosta-5-cis,13-transdienoic acid, dl-9α-fluoro-11β,15β-dihydroxy-15α-methyl- and dl-9α-fluoro-11β,15α-dihydroxy-15β-methylprosta-5-cis,13-transdienoic acid, 8R-9β-fluoro-11β,15β-dihydroxy-15α-methyl- and 8R-9β-fluoro-11β,15α-dihydroxy-15β-methylprosta-5-cis,13-transdienoic acid, and dl-9β-fluoro-11β,15β-dihydroxy-15α-methyl- and dl-9β-fluoro-11β,15α-dihydroxy-15β-methylprosta-5-cis,13-transdienoic acid, respectively, which can then be separated into the individual isomers, i.e., the methyl esters of dl-9β-fluoro-11α,15β-dihydroxy-15α-methylprosta-5-cis,13-trans-dienoic acid, dl-9β-fluoro-11α,15α-dihydroxy-15β-methylprosta-5-cis,13-trans-dienoic acid, 8R-9α-fluoro-11α,15α-dihydroxy-15α-methylprosta-5-cis,13-trans-dienoic acid, 8R-9α-fluoro-11α,15α-dihydroxy-15β-methylprosta-5-cis,13-trans-dienoic acid, dl-9α-fluoro-11α,15β-dihydroxy-15α-methylprosta-5-cis,13-trans-dienoic acid, dl-9α-fluoro-11α,15α-dihydroxy-15β-methylprosta-5-cis,13-trans-dienoic acid, 8R-9α-fluoro-11β,15β-dihydroxy-15α-methylprosta-5-cis,13-trans-dienoic acid, 8R-9α-fluoro-11β,15α-dihydroxy-15β-methylprosta-5-cis,13-trans-dienoic acid, dl-9α-fluoro-11β,15β-dihydroxy-15α-methylprosta-5-cis,13-trans-dienoic acid, dl-9α-fluoro-11β,15α-dihydroxy-15β-methylprosta-5-cis,13-trans-dienoic acid, 8R-9β-fluoro-11β,15β-dihydroxy-15α-methylprosta-5-cis,13-trans-dienoic acid, 8R-9β-fluoro-11β,15α-dihydroxy-15β-methylprosta-5-cis,13-trans-dienoic acid, dl-9β-fluoro-11β,15β-dihydroxy-15α-methylprosta-5-cis,13-trans-dienoic acid, and dl-9β-fluoro-11β,15α-dihydroxy-15β-methylprosta-5-cis,13-trans-dienoic acid, respectively.

In like manner, by substituting ethylmagnesium bromide for methylmagnesium bromide and using the appropriate dl- and 8R-ξ9 -fluoro-11ξ-trimethylsilyloxy-15-oxo methyl ester starting compound there is obtained the corresponding mixtures and individual isomers of the methyl esters of the dl- and 8R- 9ξ-fluoro-11ξ-hydroxy-15β-hydroxy-15α-ethyl compounds of Formula (29; $R^1$ = ethyl), and dl- and 8R-ξ 9 -fluoro-11ξ-hydroxy-15α-hydroxy-15α-ethyl compounds of Formula (30; $R^1$ = ethyl).

EXAMPLE 24

To a solution of 50 mg. of the methyl ester of 8R-9β-fluoro-11α,15β-dihydroxy-15α-methylprosta-5-cis,13-transdienoic acid (29; 9β-F, 11α,15β-diOH, 15α-methyl) in 0.8 ml. of methanol water is added until turbidity develops and then 43 mg. of anhydrous potassium carbonate is added. The reaction mixture is left at room temperature for 53 hours, evaporated to one-half its original volume and neutralized with 0.1N acetic acid. The neutralized mixture is extracted (4 × 40 ml.) with ethyl acetate, washed with a saturated solution of sodium potassium tartrate, dried, evaporated, and purified by thin layer chromatography on silica gel, using chloroform:methanol (90:10) as the eluting solvent. The plates are extracted with 100 ml. of methanol, and the extract obtained is evaporated to dryness, and 3 ml. of water and five drops of acetic acid are added thereto. The thus obtained solution is extracted five times with ethyl acetate: ether [(1:1); 5 ml.]. The extracts are combined and washed with 2 ml. of water and 2 ml. of a saturated sodium chloride solution, dried over magnesium sulfate and evaporated to yield 40 mg. of 8R-9β-fluoro-11α,15β-dihydroxy-15α-methylprosta-5-cis,13-trans-dienoic acid (31; 9β-F, 11α,15β-diOH, 15α-methyl) an oil, having an $[\alpha]_D^{CHCl_3}$ −42° (2 mg./1 ml.); IR: $\nu_{max}^{CHCl_3}$ 3615, 3400, 2650, 1713, 969 cm.$^{-1}$; NMR: $\delta_{TMS}^{CDCl_3}$ 0.87 (t, 3H), 1.28 (s, 3H), 2.31 (t, 2H), 4.16 (m, 4H), 4.75 (m, 1H), 5.35–5.76 (m, 4H).

Similarly, substituting the methyl esters of dl-9β-fluoro-11α,15β-dihydroxy-15α-methylprosta-5-cis,13-trans-dienoic acid, 8R-9α-fluoro-11α-15β-dihydroxy-15α-methylprosta-5-cis,13-trans-dienoic acid, dl-9α-fluoro-11α,15β-dihydroxy-15α-methylprosta-5-cis,13-trans-dienoic acid, 8R-9α-fluoro-11β,15β-dihydroxy-15α-methylprosta-5-cis,13-trans-dienoic acid, dl-9α-fluoro-11β,15β-dihydroxy-15α-methylprosta-5-cis,13-trans-dienoic acid, 8R-9β-fluoro-11β,15β-dihydroxy-15α-methylprosta-5-cis,13-trans-dienoic acid, and dl-9β-fluoro-11β,15β-dihydroxy-15α-methylprosta-5-cis,13-trans-dienoic acid, for the methyl ester of 8R-9β-fluoro-11α,15β-dihydroxy-15α-methylprosta-5-cis,13-trans-dienoic acid is productive of the corresponding free acids dl-9β-fluoro-11α,15β-dihydroxy-15α-methylprosta-5-cis,13-trans-dienoic acid, 8R-9α-fluoro-11α,15β-dihydroxy-15α-methylprosta-5-cis,13-trans-dienoic acid, dl9α-fluoro-11α,15β-dihydroxy-15α-methylprosta-5-cis,13-trans-dienoic acid, 8R-9α-fluoro-11β,15β-dihydroxy-15α-methylprosta-5-cis,13-trans-dienoic acid, dl-9α-fluoro-11β,15β-dihydroxy-15α-methylprosta-5-cis,13-trans-dienoic acid, 8R-9β-fluoro-11β,15β-dihydroxy-15α-methylprosta-5-cis,13-trans-dienoic acid, and dl-9β-fluoro-11β,15β-dihydroxy-15α-methylprosta-5-cis,13-trans-dienoic acid, respectively.

In like manner, substituting the appropriate methyl esters of the dl- and 8R-15β-hydroxy-15α-ethyl compounds (29; $R^1$ = ethyl) there are obtained the free acids, dl- and 8R-9β-fluoro-11α,15β-dihydroxy-15α-ethyl-prosta-5-cis,13-trans-dienoic acid, dl- and 8R-9α-fluoro-11α,15β-dihydroxy-15α-ethyl-prosta-5-cis,13-trans-dienoic acid, dl- and 8R-9α-fluoro-11β,15β-dihydroxy-15α-ethyl-prosta-5-cis,13-trans-dienoic acid, and dl- and 8R-9β-fluoro-11β,15β-dihydroxy-15α-ethyl-prosta-5-cis,13-trans-dienoic acid.

EXAMPLE 25

To a solution of 60 mg. of the methyl ester of 8R-9β-fluoro-11α,15α-dihydroxy-15β-methylprosta-5-cis,13-transdienoic acid (30; 9β-F, 11α, 15α-diOH, 15β-methyl) in 1 ml. of methanol water is added until turbidity develops and then 45 mg. of anhydrous potassium carbonate is added. The reaction mixture is left at room temperature for 53 hours, evaporated to one-half its original volume and neutralized with 0.1N acetic acid. The neutralized mixture is extracted (4 × 40 ml.)

with ethyl acetate, washed with a solution of sodium potassium tartrate, dried, evaporated and purified by thin layer chromatography on silica gel, using chloroform:methanol (90:10) as the eluting solvent. The plates are extracted with 100 ml. of methanol, and the extract obtained is evaporated to dryness, and 3 ml. of water and five drops of acetic acid are added thereto. The thus obtained solution is extracted five times with ethyl acetate:ether [(1:1); 5 ml.]. The extracts are combined and washed with 2 ml. of water and 2 ml. of a saturated sodium chloride solution, dried over magnesium sulfate and evaporated to yield 45 mg. of 8R-9β-fluoro-11α,15α-dihydroxy-15β-methylprosta-5-cis,13-trans-dienoic acid (32; 9β-F, 11α,15α-diOH, 15β-methyl), an oil, having an $[\alpha]_D^{CHCl_3}$ −5.7° (2.81 mg./1 ml.); IR:$\nu_{max}^{CHCl_3}$ 3615, 3400, 2640, 1713, 965 cm.$^{-1}$, NMR: $\delta_{TMS}^{CDCl_3}$ 0.86 (t, 3H), 1.26 (s, 3H), 2.31 (t, 2H), 4.12 (m, 1H), 4.68 (m, 3H), 4.75 (m, 1H), 5.35–5.70 (m, 4H).

Similarly, substituting the methyl esters of
dl-9β-fluoro-11α,15α-dihydroxy-15β-methylprosta-5-cis,13-trans-dienoic acid,
8R-9α-fluoro-11α,15α-dihydroxy-15β-methylprosta-5-cis,13-trans-dienoic acid,
dl-9α-fluoro-11α,15α-dihydroxy-15β-methylprosta-5-cis,13-trans-dienoic acid,
8R-9α-fluoro-11β,15α-dihydroxy-15β-methylprosta-5-cis,13-trans-dienoic acid,
dl-9α-fluoro-11β,15α-dihydroxy-15β-methylprosta-5-cis,13-trans-dienoic acid,
8R-9β-fluoro-11β,15α-dihydroxy-15β-methylprosta-5-cis,13-trans-dienoic acid, and
dl-9β-fluoro-11β,15α-dihydroxy-15β-methylprosta-5-cis,13-trans-dienoic acid,
for the methyl ester of 8R-9β-fluoro-11α,15α-dihydroxy-15β-methylprosta-5-cis,13trans-dienoic acid is productive of the corresponding free acids,
dl-9β-fluoro-11α,15α-dihydroxy-15β-methylprosta-5-cis,13-trans-dienoic acid,
8R-9α-fluoro-11α,15α-dihydroxy-15β-methylprosta-5-cis,13-trans-dienoic acid,
dl-9α-fluoro-11α,15αdihydroxy-15β-methylprosta-5-cis,13trans-dienoic acid,
8R-9α-fluoro-11β,15α-dihydroxy-15β-methylprosta-5-cis,13-trans-dienoic acid,
dl-9α-fluoro-11β,15α-dihydroxy-15β-methylprosta-5-cis,13-trans-dienoic acid,
8R-9β-fluoro-11β,15α-dihydroxy-15β-methylprosta-5-cis,13-trans-dienoic acid, and
dl-9β-fluoro-11β,15α-dihydroxy-15β-methylprosta-5-cis,13-trans-dienoic acid, respectively In like manner, substituting the appropriate methyl esters of the dl- and 8R-15α-hydroxy-15β-ethyl compounds (30; R$^1$ = ethyl) there are obtained the free acids,
dl- and 8R-9β-fluoro-11α,15α-dihydroxy-15β-ethyl-prosta-5-cis,13-trans-dienoic acid,
dl- and 8R-9α-fluoro-11α,15α-dihydroxy-15β-ethyl-prosta-5-cis,13-trans-dienoic acid,
dl- and 8R-9α-fluoro-11β,15α-dihydroxy-15β-ethyl-prosta-5-cis,13-trans-dienoic acid, and
dl- and 8R-9β-fluoro 11β,15α-dihydroxy-15β-ethyl-prosta-5-cis,13-trans-dienoic acid.

EXAMPLE 26

To a solution of 100 mg. of 8R-9β-fluoro-11α-15α-dihydroxyprosta-5-cis,13-trans-dienoic acid in 5 ml. of ether is added 3 ml. of an ethereal solution of diazoethane, and the reaction mixture is maintained at room temperature for 15 minutes. The solvents and excess reagent are eliminated by vacuum distillation and the residue is purified by thin layer chromatography to afford the ethyl ester of 8R-9β-fluoro-11α,15α-dihydroxyprosta-5-cis,13-trans-dienoic acid.

Similarly, by substituting the appropriate free acid starting material for 8R-9β-fluoro-11α,15α-dihydroxyprosta-5-cis,13-trans-dienoic acid is productive of the ethyl esters of, for example,
dl-9β-fluoro-11α,15α-dihydroxyprosta-5-cis-13-transdienoic acid,
8R-9α-fluoro-11α,15α-dihydroxyprosta-5-cis,13-transdienoic acid,
dl-9α-fluoro-11α,15α-dihydroxyprosta-5-cis,13-transdienoic acid,
8R-9α-fluoro-11β,15α-dihydroxyprosta-5-cis,13-transdienoic acid,
dl-9α-fluoro-11β,15α-dihydroxyprosta-5-cis,13-transdienoic acid,
8R-9β-fluoro-11β,15α-dihydroxyprosta-5-cis,13-transdienoic acid,
dl-9β-fluoro-11β,15α-dihydroxyprosta-5-cis,13-transdienoic acid,
8R-9α-fluoro-11α,15α-dihydroxy-15β-methylprosta-5-cis,13-trans-dienoic acid,
dl-9α-fluoro-11α,15α-dihydroxy-15β-methylprosta-5-cis,13-trans-dienoic acid,
8R-9α-fluoro-11α,15β-dihydroxy-15α-methylprosta-5-cis,13-trans-dienoic acid,
dl-9α-fluoro-11α,15β-dihydroxy-15α-methylprosta-5-cis,13-trans-dienoic acid,
8R-9β-fluoro-11α,15α-dihydroxy-15β-methylprosta-5-cis,13-trans-dienoic acid,
dl-9β-fluoro-11α,15α-dihydroxy-15β-methylprosta-5-cis,13-trans-dienoic acid,
8R-9β-fluoro-11α,15α-dihydroxy-15α-methylprosta-5-cis,13-trans-dienoic acid,
dl-9β-fluoro-11α,15β-dihydroxy-15α-methylprosta-5-cis,13-trans-dienoic acid,
8R-9α-fluoro-11β,15α-dihydroxy-15β-methylprosta-5-cis,13-trans-dienoic acid,
dl-9α-fluoro-11β,15α-dihydroxy-15β-methylprosta-5-cis,13-trans-dienoic acid,
8R-9α-fluoro-11β,15β-dihydroxy-15α-methylprosta-5-cis-13-trans-dienoic acid,
dl-9α-fluoro-11β,15β-dihydroxy-15α-methylprosta-5-cis-13-trans-dienoic acid,
8R-9β-fluoro-11β,15α-dihydroxy-15β-methylprosta-5-cis,13-trans-dienoic acid,
dl-9β-fluoro-11β,15α-dihydroxy-15β-methylprosta-5-cis,13-trans-dienoic acid,
8R-9β-fluoro-11β,15β-dihydroxy-15α-methylprosta-5-cis,13-trans-dienoic acid, and
dl-9β-fluoro-11β,15β-dihydroxy-15α-methylprosta-5-cis,13-trans-dienoic acid, respectively.

In like manner, substituting diazopropane (or other diazoalkane) and using the appropriate free acid starting material, there is obtained the corresponding propyl (or other alkyl) ester corresponding to the free acid starting material.

EXAMPLE 27

To a solution of 356 mg. of 8R-9β-fluoro-11α,15α-dihydroxyprosta-5-cis,13-trans-dienoic acid in 3.56 ml. of methanol is added 10 ml. of a 0.1N solution of sodium hydroxide and the mixture is stirred at room temperature for 1 hour. The reaction mixture then evaporated to dryness under reduced pressure, to give the sodium salt of 8R-9β-fluoro-11α,15α-dihydroxyprosta-5-cis,13-trans-dienoic acid.

By employing 1.1 molar equivalents of potassium hydroxide (in the form of a 0.1N solution) in place of sodium hydroxide in the above procedure the potassium salt of 8R-9β-fluoro-11α,15α-dihydroxyprosta-5-cis,13-trans-dienoic acid is obtained.

Similarly, the sodium and potassium salts of the other dl- and 8R-prostadienoic acid derivatives can be produced, e.g., the sodium (and potassium) salts of
dl-9β-fluoro-11α,15α-dihydroxyprosta-5-cis,13-transdienoic acid,
8R-9α-fluoro-11α,15α-dihydroxyprosta-5-cis,13-transdienoic acid,
dl-9α-fluoro-11α,15α-dihydroxyprosta-5-cis,13-transdienoic acid,
8R-9α-fluoro-11β,15α-dihydroxyprosta-5-cis,13-transdienoic acid,
dl-9α-fluoro-11β,15α-dihydroxyprosta-5-cis,13-transdienoic acid,
8R-9β-fluoro-11β,15α-dihydroxyprosta-5-cis,13-transdienoic acid,
dl-9β-fluoro-11β,15α-dihydroxyprosta-5-cis,13-transdienoic acid,
8R-9α-fluoro-11α,15α-dihydroxy-15β-methylprosta-5-cis,13-trans-dienoic acid,
dl-9α-fluoro-11α,15α-dihydroxy-15β-methylprosta-5-cis,13-trans-dienoic acid,
8R-9α-fluoro-11α,15β-dihydroxy-15α-methylprosta-5-cis,13-trans-dienoic acid,
dl-9α-fluoro-11α,15β-dihydroxy-15α-methylprosta-5-cis,13-trans-dienoic acid,
8R-9β-fluoro-11α,15α-dihydroxy-15β-methylprosta-5-cis,13-trans-dienoic acid,
dl-9β-fluoro-11α,15α-dihydroxy-15β-methylprosta-5-cis,13-trans-dienoic acid,
8R-9β-fluoro-11α,15β-dihydroxy-15α-methylprosta-5-cis,13-trans-dienoic acid,
dl-9β-fluoro-11α,15β-dihydroxy-15α-methylprosta-5-cis,13-trans-dienoic acid,
8R-9α-fluoro-11β,15α-dihydroxy-15β-methylprosta-5-cis,13-trans-dienoic acid,
dl-9α-fluoro-11β,15α-dihydroxy-15β-methylprosta-5-cis,13-trans-dienoic acid,
8R-9α-fluoro-11β,15β-dihydroxy-15α-methylprosta-5-cis,13-trans-dienoic acid,
dl-9α-fluoro-11β,15β-dihydroxy-15α-methylprosta-5-cis,13-trans-dienoic acid,
8R-9β-fluoro-11β,15α-dihydroxy-15β-methylprosta-5-cis,13-trans-dienoic acid,
dl-9β-fluoro-11β,15α-dihydroxy-15β-methylprosta-5-cis,13-trans-dienoic acid,
8R-9β-fluoro-11β,15β-dihydroxy-15α-methylprosta-5-cis,13-trans-dienoic acid, and dl-9β-fluoro-11β,15β-dihydroxy-15α-methylprosta-5-cis,13-trans-dienoic acid, respectively.

EXAMPLE 28

To a solution of 356 mg. of 8R-9β-fluoro-11α,15α-dihydroxyprosta-5-cis,13-trans-dienoic acid in 3.56 ml. of methanol is added a mixture of 1 ml. of concentrated ammonium hydroxide solution and 2 ml. of methanol. The resulting mixture is stirred for 2 hours at room temperature and then evaporated to dryness, to yield the ammonium salt of 8R-9β-fluoro-11α,15α-dihydroxyprosta-5-cis,13-transdienoic acid.

By employing dimethylamine, diethylamine or dipropylamine in place of ammonium hydroxide in the above procedure, the corresponding salts of 8R-9β-fluoro-11α,15α-dihydroxyprosta-5-cis,13-trans-dienoic acid are obtained.

In a similar manner, the ammonium, dimethylamine, diethylamine and dipropylamine salts of the other dl- and 8R-prostadienoic acid derivatives,
dl-9β-fluoro-11α,15α-dihydroxyprosta-5-cis,13-transdienoic acid,
8R-9α-fluoro-11α,15α-dihydroxyprosta-5-cis,13-transdienoic acid,
dl-9α-fluoro-11α,15α-dihydroxyprosta-5-cis,13-transdienoic acid,
8R-9α-fluoro-11β,15α-dihydroxyprosta-5-cis,13-transdienoic acid,
dl-9α-fluoro-11β,15α-dihydroxyprosta-5-cis,13-transdienoic acid,
8R-9β-fluoro-11β,15α-dihydroxyprosta-5-cis,13-transdienoic acid,
dl-9β-fluoro-11β,15α-dihydroxyprosta-5-cis,13-transdienoic acid,
8R-9α-fluoro-11α,15α-dihydroxy-15β-methylprosta-5-cis,13-trans-dienoic acid,
dl-9α-fluoro-11α,15α-dihydroxy-15β-methylprosta-5-cis,13-trans-dienoic acid,
8R-9α-fluoro-11α,15β-dihydroxy-15αmethylprosta-5-cis,13-trans-dienoic acid,
dl-9α-fluoro-11α,15β-dihydroxy-15αmethylprosta-5-cis,13-trans-dienoic acid,
8R-9β-fluoro-11α,15α-dihydroxy-15β-methylprosta-5-cis,13-trans-dienoic acid,
dl-9β-fluoro-11α,15α-dihydroxy-15β-methylprosta-5-cis,13-trans-dienoic acid,
8R-9β-fluoro-11α,15β-dihydroxy-15α-methylprosta-5-cis,13-trans-dienoic acid,
dl-9β-fluoro-11α,15β-dihydroxy-15α-methylprosta-5-cis,13-trans-dienoic acid,
8R-9α-fluoro-11β, 15α-dihydroxy-15β-methylprosta-5-cis,13-trans-dienoic acid,
dl-9α-fluoro-11β,15α-dihydroxy-15β-methylprosta-5-cis,13-trans-dienoic acid,
8R-9α-fluoro-11β,15β-dihydroxy-15α-methylprosta-5-cis,13-trans-dienoic acid,
dl-9α-fluoro-11β,15β-dihydroxy-15α-methylprosta-5-cis,13-trans-dienoic acid,
8R-9β-fluoro-11β,15α-dihydroxy-15β-methylprosta-5-cis,13-trans-dienoic acid,
dl-9β-fluoro-11β,15α-dihydroxy-15β-methylprosta-5-cis,13-trans-dienoic acid,
8R-9β-fluoro-11β,15β-dihydroxy-15α-methylprosta-5-cis,13-trans-dienoic acid, and
dl-9β-fluoro-11β,15β-dihydroxy-15α-methylprosta-5cis,13-trans-dienoic acid, are prepared.

EXAMPLE 29

To a mixture of 236 mg. of procaine and 3.5 ml. of aqueous methanol is added 356 mg. of 8R-9β-fluoro-11α,15α-dihydroxyprosta-5-cis,13-trans-dienoic acid in 3.56 ml. of methanol and the resultant reaction mixture is stirred at room temperature for two hours. It is then evaporated to dryness under reduced pressure to give the procaine salt of 8R-9β-fluoro-11α,15α-dihydroxyprosta-5-cis,13-transdienoic acid.

Similarly, the lysine, caffeine and arginine salts thereof are obtained.

In like manner, the procaine, lysine, caffeine and arginine salts of the other dl- and 8R-prostadienoic acid derivatives, dl-9β-fluoro-11α,15α-dihydroxyprosta-5-cis,13-transdienoic acid, 8R-9α-fluoro-11α,15α-dihydroxyprosta-5-cis,13-transdienoic acid, dl-9α-fluoro-11α,15α-dihydroxyprosta-5-cis,13-transdienoic acid, 8R-9α-fluoro-11β,15α-dihydroxyprosta-5-cis,13-transdienoic acid, dl-9α-fluoro-11β,15α-dihydroxyprosta-5-cis,13-transdienoic acid, 8R-9β-fluoro-11β,15α-dihydroxyprosta-5-cis,13-transdienoic acid, dl-9βfluoro-11β,15α-dihydroxyprosta-5-cis,13-transdienoic acid, 8R-9α-fluoro-11α,15α-dihydroxy-15β-methylprosta-5-cis,13-trans-dienoic acid, dl-9α-fluoro-11α,15α-dihydroxy-15β-methylprosta-5-cis,13-trans-dienoic acid, 8R-9α-fluoro-11α,15β-dihydroxy-15α-methylprosta-5-cis,13-trans-dienoic acid, dl-9α-fluoro-11α,15β-dihydroxy-15α-methylprosta-5-cis,13-trans-dienoic acid, 8R-9β-fluoro-11α,15α-dihydroxy-15β-methylprosta-5-cis,13-trans-dienoic acid, dl-9β-fluoro-11α,15α-dihydroxy-15β-methylprosta-5-cis,13-trans-dienoic acid, 8R-9β-fluoro-11α,15β-dihydroxy-15α-methylprosta-5-cis,13-trans-dienoic acid, dl-9β-fluoro-11α,15β-dihydroxy-15α-methylprosta-5-cis,13-trans-dienoic acid, 8R-9α-fluoro-11β,15α-dihydroxy-15β-methylprosta-5cis,13-trans-cienoic acid, dl-9α-fluoro-11β,15α-dihydroxy-15β-methylprosta-5cis,13-trans-dienoic acid, 8R-9α-fluoro-11β,15α-dihydroxy-15α-methylprosta-5cis,13-trans-dienoic acid, dl-9α-fluoro-11β,15α-dihydroxy-15α-methylprosta-5cis,13-trans-dienoic acid, 8R-9β-fluoro-11β,15α-dihydroxy-15β-methylprosta-5cis,13-trans-dienoic acid, dl-9β-fluoro-11β,15α-dihydroxy-15β-methylprosta-5cis,13-trans-dienoic acid, 8R-9β-fluoro-11β,15β-dihydroxy-15α-methylprosta-5cis,13-trans-dienoic acid, and dl-9β-fluoro-11β,15β-dihydroxy-15α-methylprosta-5-cis,13-trans-dienoic acid, are prepared.

EXAMPLE 30

A solution of 14 mg. of tromethamine in 0.03 ml. of water at 60° C. is added with vigorous stirring to a solution of 50 mg. of 8R-9β-fluoro-11α,15α-dihydroxyprosta-5-cis,13-trans-dienoic acid in 7 ml. of acetonitrile which has just been brought to the boiling point. The vessel which contained the aqueous tromethamine solution is rinsed with 0.03 ml. of water. The solution is cooled to room temperature and then left at 25° C. for 12 hours and then refrigerated to −10° C. for 24 hours. The solvent is removed under vacuum, 1 ml. of acetonitrile is added and then 2 ml. of ether is added. After standing for 48 hours at −10° C. the crystalline salt which forms is separated by filtration, washed three times with ether and then dried under vacuum to yield 45 mg. of the tromethamine salt of 8R-9β-fluoro-11α,15α-dihydroxyprosta-5-cis,13-transdienoic acid, melting point 86 - 87° C.; IR: $\nu_{max}^{film}$ 3280, 1560, 962 cm.$^{-1}$.

In like manner, by substituting the appropriate free acid starting material for 8R-9β-fluoro-11α,15α-dihydroxyprosta-5-cis,13-trans-dienoic acid there is obtained the tromethamine salt of, dl-9β-fluoro-11α,15α-dihydroxyprosta-5-cis,13-transdienoic acid, 8R-9α-fluoro-11α,15α-dihydroxyprosta-5-cis,13-transdienoic acid.

dl-9α-fluoro-11α,15α-dihydroxyprosta-5-cis,13-transdienoic acid,

8-R-9αfluoro-11β,15α-dihydroxyprosta-5-cis,13-transdienoic acid, dl-9α-fluoro-11β,15α-dihydroxyprosta-5-cis,13-transdienoic acid, 8R-9β-fluoro-11β,15α-dihydroxyprosta-5-cis,13-transdienoic acid, dl-9β-fluoro-11β,15α-dihydroxyprosta-5-cis,13-transdienoic acid.

8R-9α-fluoro-11α,15α-dihydroxy-15β-methylprosta-5-cis,13-trans-dienoic acid, dl-9α-fluoro-11α,15α-dihydroxy-15β-methylprosta-5-cis,13-trans-dienoic acid, 8R-9α-fluoro-11α,15β-dihydroxy-15α-methylprosta-5-cis,13-trans-dienoic acid, dl-9α-fluoro-11α,15β-dihydroxy-15α-methylprosta-5-cis,13-trans-dienoic acid, 8R-9β-fluoro-11α,15α-dihydroxy-15β-methylprosta-5-cis,13-trans-dienoic acid, dl-9β-fluoro-11α,15α-dihydroxy-15β-methylprosta-5-cis,13-trans-dienoic acid, 8R-9β-fluoro-11α,15β-dihydroxy-15α-methylprosta-5-cis,13-trans-dienoic acid, dl-9β-fluoro-11α,15β-dihydroxy-15α-methylprosta-5-cis,13-trans-dienoic acid, 8R-9α-fluoro-11β,15α-dihydroxy-15β-methylprosta-5-cis,13-trans-dienoic acid, dl-9α-fluoro-11β,15α-dihydroxy-15β-methylprosta-5-cis,13-trans-dienoic acid, 8-R-9α-fluoro-11β,15β-dihydroxy-15α-methylprosta-5-cis,13-trans-dienoic acid, dl-9α-fluoro-11β,15β-dihydroxy-15α-methylprosta-5-cis,13-trans-dienoic acid, 8R-9β-fluoro-11β,15α-dihydroxy-15β-methylprosta-5-cis,13-trans-dienoic acid.

dl-9β-fluoro-11β,15α-dihydroxy-15βmethylprosta-5-cis,13-trans-dienoic acid, 8R-9β-fluoro-11β,15β-dihydroxy-15α-methylprosta-5-cis,13-trans-dienoic acid, and dl-9βfluoro-11β,15β-dihydroxy-15α-methylprosta-5-cis,13-trans-dienoic acid.

EXAMPLE 31

AEROSOL BRONCHODILATOR TEST IN THE GUINEA PIG (HISTAMINE CHALLENGE)

Test Animal: Female guinea pig, 400–500 g.
Vehicle: Buffered saline.

Procedure: The animals are anesthetized with urethane (1 g./kg., intraperitoneally) and both the trachea and a jugular vein are cannulated. The tracheal cannula (plastic tube) is attached to a Harvard ventilator and pressure transducer to measure changes in respiratory resistance. The jugular cannula (a 22 gauge needle) permits injection of the intravenously administered materials. Recording is done via a Harvard Biograph. A standard histamine challenge is given to determine the animal's sensitivity to histamine. Five minutes later the test material is given by aerosol followed by a second histamine challenge after dosing with the test material. Repeated histamine challanges are given to determine duration of action of the test material.

As measured by this assay, 8R-9β-fluoro-11α,15α-dihydroxyprosta-5-cis,13-trans-dienoic acid has twice the activity of $PGE_2$ and 8R-9β-fluoro-11α,15α-dihydroxy-15β-methylprosta-5-cis,13-trans-dienoic acid has about twice the activity of $PGE_2$.

EXAMPLE 32

INTRAVENOUS BRONCHODILATOR TEST IN THE GUINEA PIG (HISTAMINE CHALLENGE)

Test Animal: Female guinea pig, 400-500 g.
Vehicle: Buffered saline.
Procedure: The animals are anesthetized with urethane (1 g./kg., intraperitoneally) and both the trachea and a jugular vein are cannulated. The tracheal cannula (plastic tube) is attached to a Harvard ventilator and pressure transducer to measure changes in respiratory resistance. The jugular cannula (a 22 gauge needle) permits injection of the intravenously administered materials. Recording is done via a Harvard Biograph. A standard histamine challange is given to determine the animal's sensitivity to histamine. Five minutes later the test material is given intravenously followed by a second histamine challange after dosing with the test material. Repeated histamine challenges are given to determine duration of action of the test material.

As measured by this assay, 8R-9β-fluoro-11α,15α-dihydroxyprosta-5-cis,13-trans-dienoic acid has about four times the activity of $PGE_2$ and 8R-9β-fluoro-11α,15α-dihydroxy-15β-methylprosta-5-cis,13-trans-dienoic acid has four times the activity of $PGE_2$.

What is claimed is:

1. A dl- or 8R-antimeric compound selected from those of the formulas:

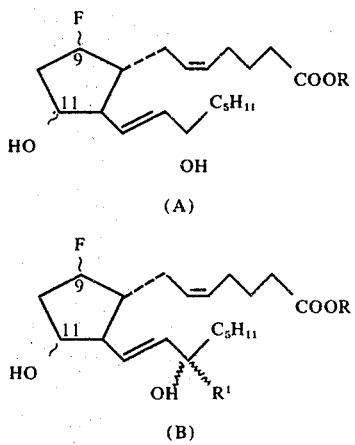

(A)

(B)

wherein R is hydrogen, a lower alkyl group of one to six carbon atoms, or the pharmaceutically acceptable, nontoxic salts of compounds in which R is hydrogen;
$R^1$ is methyl or ethyl; and
the wavy lines ($\xi$) represent the α or β configuration or mixtures thereof, provided that when $R^1$ is α, the hydroxyl group, attached to the same carbon atom as $R^1$, is β; and when $R^1$ is β, the hydroxyl group, attached to the same carbon as $R^1$, is α.

2. A compound according to Formula (A) of claim 1 wherein the 9-fluoro is α and the 11-hydroxyl is α.
3. A compound according to Formula (A) of claim 1 wherein the 9-fluoro is β and the 11-hydroxyl is α.
4. A compound according to Formula (A) of claim 1 wherein the 9-fluoro is α and the 11-hydroxyl is β.
5. A compound according to Formula (A) of claim 1 wherein the 9-fluoro is β and the 11-hydroxyl is β.
6. A compound according to Formula (B) of claim 1 wherein the 9-fluoro is α, the 11-hydroxyl is α, the 15-hydroxyl is α, and $R^1$ is β.
7. A compound according to Formula (B) of claim 1 wherein the 9-fluoro is α, the 11-hydroxyl is α, the 15-hydroxyl is β, and $R^1$ is α.
8. A compound according to Formula (B) of claim 1 wherein the 9-fluoro is β, the 11-hydroxyl is α, the 15-hydroxyl is α, and $R^1$ is β.
9. A compound according to Formula (B) of claim 1 wherein the 9-fluoro is β, 11-hydroxyl is α, the 15-hydroxyl is β, and $R^1$ is α.
10. A compound according to Formula (B) of claim 1 wherein the 9-fluoro is α, the 11hydroxyl is β, the 15-hydroxyl is α, and $R^1$ is β.
11. A compound according to Formula (B) of claim 1 wherein the 9-fluoro is α, the 11-hydroxyl is β, the 15-hydroxyl is β, and $R^1$ is α.
12. A compound according to Formula (B) of claim 1 wherein the 9-fluoro is β, 11-hydroxyl is β, the 15-hydroxyl is α, and $R^1$ is β.
13. A compound according to Formula (B) of claim 1 wherein the 9-fluoro is β, the 11-hydroxyl is β, the 15-hydroxyl is β, and $R^1$ is α.
14. The 8R compound according to claim 2 wherein R is hydrogen; 8R-9α-fluoro-11α,15α-dihydroxyprosta-5-cis,13-trans-dienoic acid.
15. The 8R compound according to claim 3 wherein R is hydrogen; 8R-9β-fluoro-11α,15α-dihydroxyprosta-5-cis,13-trans-dienoic acid.
16. The 8R compound according to claim 4 wherein R is hydrogen; 8R-9α-fluoro-11β,15α-dihydroxyprosta-5-cis,13-trans-dienoic acid.
17. The 8R compound according to claim 5 wherein R is hydrogen; 8R-9β-fluoro-11β,15α-dihydroxyprosta-5-cis,13-trans-dienoic acid.
18. The 8R compound according to claim 6 wherein R is hydrogen and $R^1$ is methyl; 8R-9α-fluoro-11α,15α-dihydroxy-15β-methylprosta-5-cis,13-trans-dienoic acid.
19. The 8R compound according to claim 7 wherein R is hydrogen and $R^1$ is methyl; 8R-9α-fluoro-11α,15β-dihydroxy-15α-methylprosta-5-cis,13-trans-dienoic acid.
20. The 8R compound according to claim 8 wherein R is hydrogen and $R^1$ is methyl; 8R-9β-fluoro-11α,15α-dihydroxy-15β-methylprosta-5-cis,13-trans-dienoic acid.
21. The 8R compound according to claim 9 wherein R is hydrogen and $R^1$ is methyl; 8R-9β-fluoro-11α,15β-dihydroxy-15α-methylprosta-5-cis,13-trans-dienoic acid.
22. The 8R compound according to claim 10 wherein R is hydrogen and $R^1$ is methyl; 8R-9α-fluoro-11β,15α-dihydroxy-15β-methylprosta-5-cis,13-trans-dienoic acid.
23. The 8R compound according to claim 11 wherein R is hydrogen and $R^1$ is methyl; 8R-9α-fluoro-11β,15β-dihydroxy-15α-methylprosta-5-cis,13-trans-dienoic acid.

24. The 8R compound according to claim 12 wherein R is hydrogen and $R^1$ is methyl; 8R-9β-fluoro-11β,15α-dihydroxy-15β-methylprosta-5-cis,13-trans-dienoic acid.

25. The 8R compound according to claim 13 wherein R is hydrogen and $R^1$ is methyl; 8R-9β-fluoro-11β,15β-dihydroxy-15α-methylprosta-5-cis,13-trans-dienoic acid.

26. The 8R compound according to claim 2 wherein R is methyl; the methyl ester of 8R-9α-fluoro-11α,15α-dihydroxyprosta-5-cis,13-trans-dienoic acid.

27. The 8R compound according to claim 3 wherein R is methyl; the methyl ester of 8R-9β-fluoro-11α,15α-dihydroxyprosta-5-cis,13-trans-dienoic acid.

28. The 8R compound according to claim 4 wherein R is methyl; the methyl ester of 8R-9α-fluoro-11β,15α-dihydroxyprosta-5-cis,13-trans-dienoic acid.

29. The 8R compound according to claim 5 wherein R is methyl; the methyl ester of 8R-9β-fluoro-11β,15α-dihydroxyprosta-5-cis,13-trans-dienoic acid.

30. The 8R compound according to claim 6 wherein each of R and $R^1$ are methyl; the methyl ester of 8R 9α-fluoro-11α,15α-dihydroxy-15β-methylprosta-5-cis,13-trans-dienoic acid.

31. The 8R compound according to claim 7 wherein each of R and $R^1$ are methyl; the methyl ester of 8R-9α-fluoro-11α,15β-dihydroxy-15α-methylprosta-5-cis,13-trans-dienoic acid.

32. The 8R compound according to claim 8 wherein each of R and $R^1$ are methyl; the methyl ester of 8R-9β-fluoro-11α,15α-dihydroxy-15β-methylprosta-5-cis,13-trans-dienoic acid.

33. The 8R compound according to claim 9 wherein each of R and $R^1$ are methyl; the methyl ester of 8R-9β-fluoro-11α,15β-dihydroxy-15α-methylprosta-5-cis,13-trans-dienoic acid.

34. The 8R compound according to claim 10 wherein each of R and $R^1$ are methyl; the methyl ester of 8R-9α-fluoro-11β,15α-dihydroxy-15β-methylprosta-5-cis,13-trans-dienoic acid.

35. The 8R compound according to claim 11 wherein each of R and $R^1$ are methyl; the methyl ester of 8R-9α-fluoro-11β,15β-dihydroxy-15α-methylprosta-5-cis,13-trans-dienoic acid.

36. The 8R compound according to claim 12 wherein each of R and $R^1$ are methyl; the methyl ester of 8R-9β-fluoro-11β,15α-dihydroxy-15β-methylprosta-5-cis,13-trans-dienoic acid.

37. The 8R compound according to claim 13 wherein each of R and $R^1$ are methyl; the methyl ester of 8R-9β-fluoro-11β,15β-dihydroxy-15α-methylprosta-5-cis,13-trans-dienoic acid.

38. The 8R compound according to claim 3; the tromethamine salt of 8R-9β-fluoro-11α,15α-dihydroxyprosta-5-cis,13-trans-dienoic acid.

39. The dl compound according to claim 3 wherein R is hydrogen; dl-9β-fluoro-11α,15α-dihydroxyprosta-5-cis,13-trans-dienoic acid.

40. The dl compound according to claim 8 wherein R is hydrogen and $R^1$ is methyl; dl-9β-fluoro-11α,15α-dihydroxy-15β-methylprosta-5-cis,13-trans-dienoic acid.

41. The dl compound according to claim 3; the tromethamine salt of dl-9β-fluoro-11α,15α-dihydroxyprosta-5-cis,13-trans-dienoic acid.

* * * * *

UNITED STATES PATENT AND TRADEMARK OFFICE
CERTIFICATE OF CORRECTION

PATENT NO. : 3,997,587
DATED : December 14, 1976
INVENTOR(S) : JOSEPH M. MUCHOWSKI et al It is certified that error appears in the above-identified patent and that said Letters Patent are hereby corrected as shown below:

Column 13, line 14, "magnesium" should read --- magnesium, ---.
Column 16, line 12, "dihydroxyprosta5" should read --- dihydroxy-prosta-5 ---. Column 17, line 1, "15αbis" should read --- 15α-bis ---. Column 17, lines 36 and 37 "oxol-1α," should read --- oxo-11α, ---. Column 18, line 24, "dl9" should read --- dl-9 ---.
Column 22, line 33, "(m, 2);" should read --- (m, 2H); ---.
Column 26, line 29, "transdienoic" should read --- trans-dienoic ---. Column 29, line 45, "8R-⌊9" should read --- 8R- 9⌊ ---.
Column 29, line 51, "8R-⌊9" should read --- 8R 9⌊---. Column 30, line 36, "dl9α" should read --- dl-9α ---. Column 31, line 36, "13trans" should read --- 13-trans ---. Column 31, lines 42 and 43, "15αdihydroxy" should read --- 15α-dihydroxy and "13trans" should read --- 13-trans ---. Column 34, line 28, "15α" should read --- 15α- ---. Column 34, line 30, "15α" should read --- 15α- ---. Column 34, line 56, "5cis" should read --- 5-cis ---.
Column 36, line 12, "8-R-9α" should read --- 8R-9α- ---.
Column 37, Claim 1, Formula (A) that portion

UNITED STATES PATENT OFFICE
CERTIFICATE OF CORRECTION

Patent No. 3,997,587  Dated December 14, 1976

Inventor(s) JOSEPH M. MUCHOWSKI et al

It is certified that error appears in the above-identified patent and that said Letters Patent are hereby corrected as shown below:

"  "   should read   --- 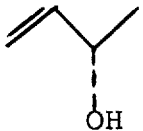 ---

OH

Column 38, Claim 10, line 22, "11hydroxyl" should read --- 11-hydroxyl ---. Column 38, Claim 12, line 28, "β,11" should read --- β, the 11 ---.

Signed and Sealed this

Seventh Day of February 1978

[SEAL]

Attest:

RUTH C. MASON  
Attesting Officer

LUTRELLE F. PARKER  
Acting Commissioner of Patents and Trademarks